United States Patent
Rauh et al.

(10) Patent No.: US 10,550,114 B2
(45) Date of Patent: Feb. 4, 2020

(54) KINASE INHIBITORS AND THEIR USE IN CANCER THERAPY

(71) Applicant: TECHNISCHE UNIVERSITÄT DORTMUND, Dortmund (DE)

(72) Inventors: Daniel Rauh, Dortmund (DE); Rajesh Gontla, Dortmund (DE); Jörn Weisner, Herten (DE)

(73) Assignee: TECHNISCHE UNIVERSITÄT DORTMUND, Dortmund (DE)

( * ) Notice: Subject to any disclaimer, the term of this patent is extended or adjusted under 35 U.S.C. 154(b) by 0 days.

(21) Appl. No.: 15/571,312

(22) PCT Filed: May 3, 2016

(86) PCT No.: PCT/EP2016/059918
§ 371 (c)(1),
(2) Date: Nov. 2, 2017

(87) PCT Pub. No.: WO2016/177746
PCT Pub. Date: Nov. 10, 2016

(65) Prior Publication Data
US 2018/0354941 A1    Dec. 13, 2018

(30) Foreign Application Priority Data
May 5, 2015 (EP) .................... 15166458

(51) Int. Cl.
*C07D 471/04* (2006.01)
*A61P 35/00* (2006.01)
*G01N 33/574* (2006.01)

(52) U.S. Cl.
CPC ............ *C07D 471/04* (2013.01); *A61P 35/00* (2018.01); *G01N 33/57484* (2013.01)

(58) Field of Classification Search
CPC .................................................. C07D 471/04
See application file for complete search history.

(56) References Cited

FOREIGN PATENT DOCUMENTS

| EP | 2810648 A1 * | 12/2014 | .......... C07D 487/04 |
|---|---|---|---|
| WO | WO-2005100356 A1 * | 10/2005 | .......... C07D 471/04 |
| WO | WO2006065601 A2 | 6/2006 | |
| WO | WO2006135627 A2 | 12/2006 | |

OTHER PUBLICATIONS

Van der Westhuizen "Synthesis of potentially irreversible Akt inhibitors" Master's Thesis, Stellenbosch University, Apr. 2014.*
Nitulescu "Akt inhibitors in cancer treatment: The long journey from drug discovery to clinical use (Review)" International Journal of Oncology 48: 869-885, 2016.*
Kettle et al. "Diverse Heterocyclic Scaffolds as Allosteric Inhibitors of AKT", Journal of Medicinal Chemistry, American Chemical Society, vol. 55, No. 3, pp. 1261-1273 (Feb. 9, 2012).
International Search Report from International Application No. PCT/EP2016/059918, dated May 30, 2016.

* cited by examiner

*Primary Examiner* — David K O'Dell
(74) *Attorney, Agent, or Firm* — Davidson, Davidson & Kappel, LLC

(57) ABSTRACT

The present invention relates to a 2,3-diphenyl-1,6-naphthyridine-5-one derivative according to general formula (I), and the use of the 2,3-diphenyl-1,6-naphthyridine-5-one derivative in the diagnosis or treatment of cancer.

8 Claims, 10 Drawing Sheets

Figure 5
a)
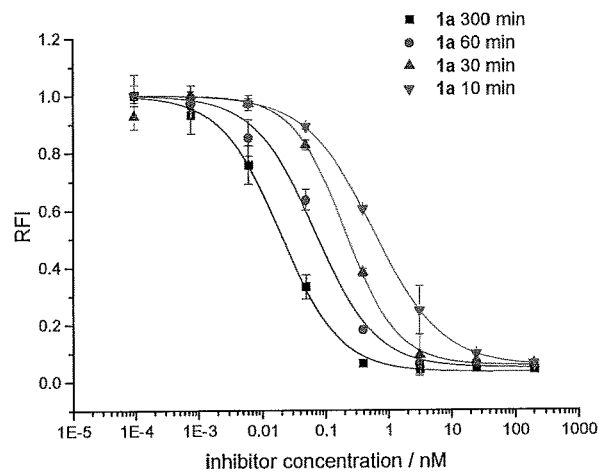
b)
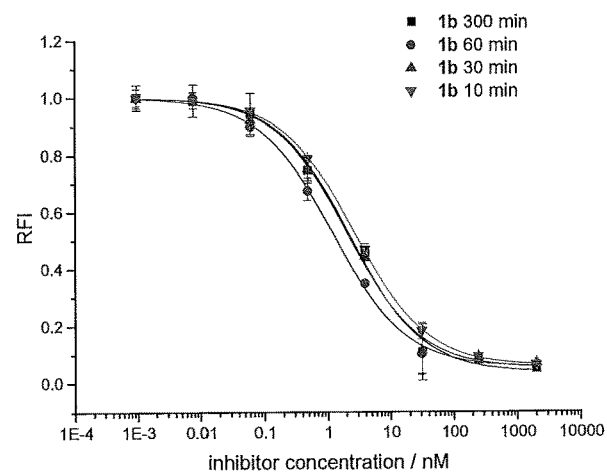
c)
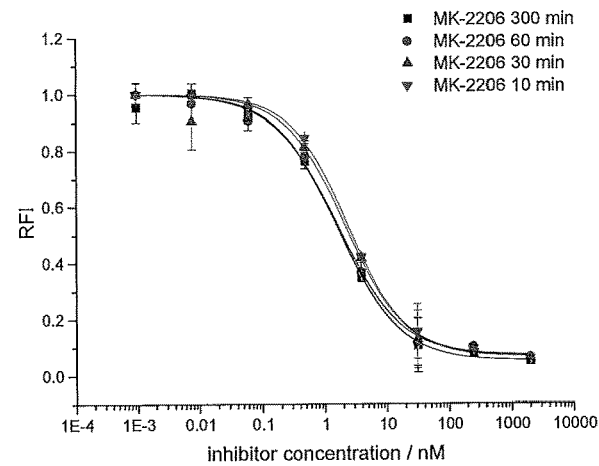

Figure 6
a)
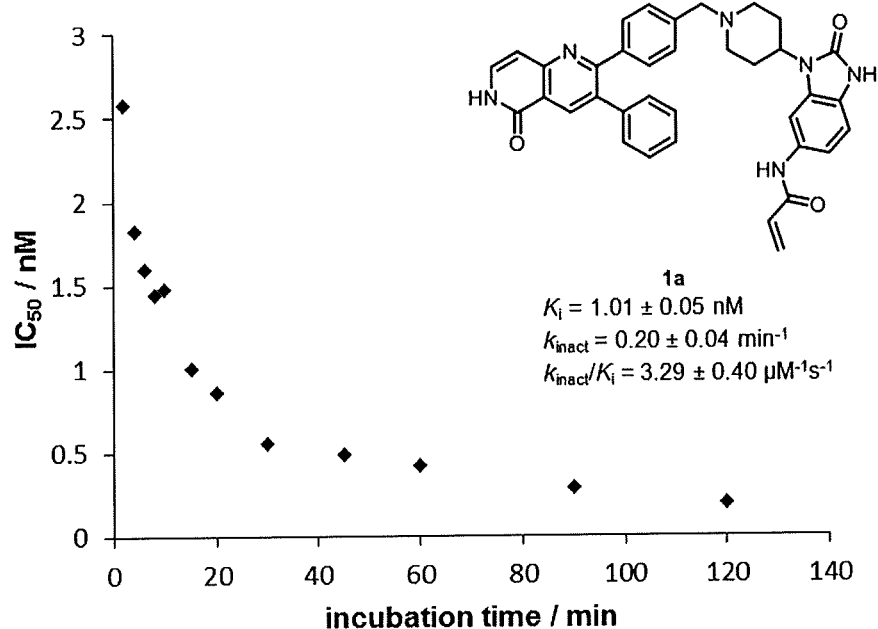
b)
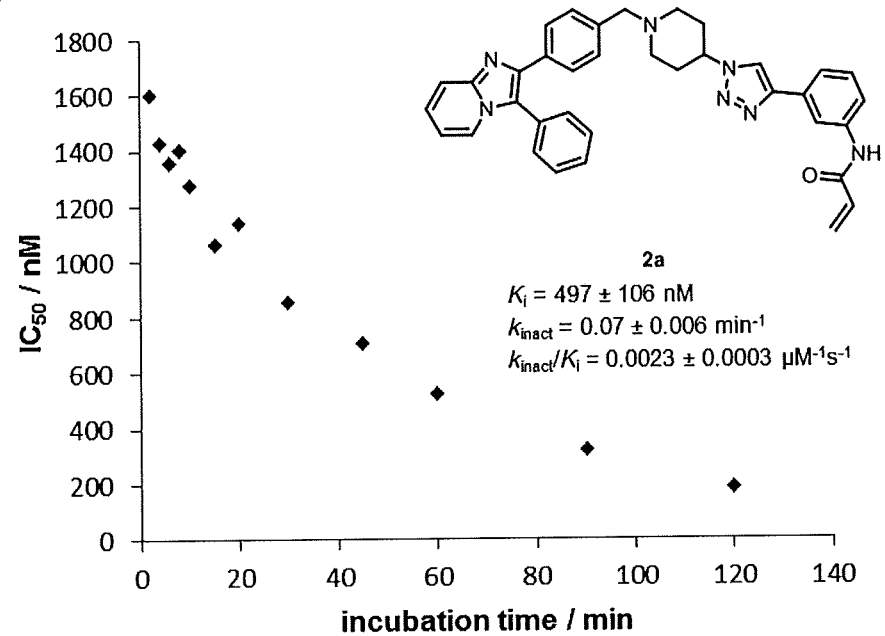

Figure 7

| Kinase | % inhibition at 1 µM of 1a | Kinase | % inhibition at 1 µM of 1a |
| --- | --- | --- | --- |
| AKT1 (PKB alpha)[a,b,c,d] | 98 | PTK2 (FAK) | 4 |
| AKT2 (PKB beta)[a,b,c,d] | 96 | CDK1/cyclin B | 3 |
| AKT3 (PKB gamma)[a,b,c,d] | 83 | MAPK1 (ERK2) | 3 |
| MAP4K5 (KHS1) | 37 | PRKX[d] | 3 |
| PRKCQ (PKC theta)[a,c,d] | 35 | ABL1 | 2 |
| MAPKAPK2[d] | 30 | CDC42 BPA (MRCKA)[b*,c] | 2 |
| MELK[c,d] | 30 | EGFR (ErbB1) | 2 |
| FGFR1 | 25 | GRK6[a] | 2 |
| RPS6KA3 (RSK2)[a,d] | 21 | PRKG2 (PKG2)[a] | 2 |
| AMPK A2/B1/G1[d] | 20 | RPS6KA5 (MSK1)[a,d] | 2 |
| GSK3B (GSK3 beta) | 20 | RPS6KB1 (p70S6K)[c,d] | 2 |
| SGK (SGK1)[c,d] | 20 | SGKL (SGK3)[c,d] | 2 |
| FLT3 | 17 | CDC42 BPB (MRCKB)[b*,c] | 1 |
| MAPKAPK3[d] | 17 | CDK2/cyclin A | 1 |
| PRKCG (PKC gamma)[a,c,d] | 17 | STK3 (MST2) | 1 |
| AURKA (Aurora A)[d] | 15 | DNA-PK | 0 |
| PASK[d] | 15 | PIM1 | 0 |
| AMPK A1/B1/G1[d] | 14 | ITK[b] | -1 |
| PRKCN (PKD3)[b] | 14 | MAPK14 (p38 alpha) Direct | -1 |
| RPS6KA2 (RSK3)[a,d] | 14 | PRKCE (PKC epsilon)[a,c,d] | -1 |
| RPS6KA6 (RSK4)[a,d] | 14 | PRKCZ (PKC zeta)[a,c,d] | -1 |
| TEK (Tie2)[b*] | 13 | STK4 (MST1) | -1 |
| CAMK4 (CaMKIV)[d] | 12 | ALK | -2 |
| RPS6KA1 (RSK1)[a,d] | 12 | DCAMKL2 (DCK2)[d] | -2 |
| PRKCA (PKC alpha)[a,c,d] | 10 | GRK5[a] | -2 |
| PRKD1 (PKC mu)[a,b] | 10 | MARK2[d] | -2 |
| SRC | 10 | MET (cMet) | -2 |
| CAMK1D (CaMKI delta)[d] | 9 | PRKCH (PKC eta)[a,c,d] | -2 |
| PRKCB2 (PKC beta II)[a,c,d] | 9 | ERBB2 (HER2) | -3 |
| ROCK1[b*,c] | 9 | MAPK3 (ERK1) | -3 |
| GRK4[a] | 8 | PLK1[d] | -3 |
| KIT | 8 | PRKACA (PKA)[a] | -3 |
| LCK | 8 | ROCK2[b*,c] | -3 |
| MKNK1 (MNK1)[d] | 8 | SYK | -3 |
| NEK1 | 8 | CHEK1 (CHK1)[d] | -4 |
| RPS6KA4 (MSK2)[a,d] | 8 | IGF1R | -4 |
| TXK | 8 | PDK1 Direct[b] | -4 |
| AURKB (Aurora B)[d] | 7 | PKN1 (PRK1)[a,c,d] | -4 |
| BMX[b] | 7 | GRK7[a] | -6 |
| BRSK1 (SAD1)[d] | 7 | MARK1 (MARK)[d] | -7 |
| EPHB4 | 7 | PRKCB1 (PKC beta I)[a,c,d] | -7 |
| PAK4[c] | 7 | JAK2 | -8 |
| RET | 7 | PRKCD (PKC delta)[a,c,d] | -8 |
| BTK[b] | 6 | FRAP1 (mTOR) | -9 |
| PRKCI (PKC iota)[a,c,d] | 6 | PAK1[c] | -9 |
| SGK2[c,d] | 6 | JAK3 | -11 |
| TBK1 | 6 | EPHA2 | -12 |
| PRKD2 (PKD2)[b] | 5 | PDGFRA (PDGFR alpha) | -12 |
| PRKG1[a] | 5 | ACVR1B (ALK4) | -13 |
| CHEK2 (CHK2)[d] | 4 | NTRK2 (TRKB) | -15 |

[a] The kinase belongs to the AGC kinase family. [b] In addition to the kinase domain, the enzyme also comprises a PH domain. [b*] Although the full-length enzyme features a regulatory PH domain, the protein construct utilized for compound profiling did not comprise such domain. [c] Kinase contains a cysteine analogous to Cys296 of Akt1. [d] Kinase contains a cysteine analogous to Cys310 of Akt1.

KINASE INHIBITORS AND THEIR USE IN CANCER THERAPY

This application is a U.S. national phase application under 35 U.S.C. of § 371 of International Application No. PCT/EP2016/059918, filed May 3, 2016, which claims priority of European Patent No. 15166458.8, filed May 5, 2015, the disclosure of which is hereby incorporated by reference herein.

The present invention relates to kinase inhibitors and their use in cancer therapy.

Cancer is a leading cause of death worldwide, and the understanding of underlying mechanisms and development of efficient and targeted therapies is of central importance. Dysregulation of kinase activity has emerged as a major mechanism by which cancer cells evade normal physiological constraints on growth and survival. Within the last two decades, kinases have evolved as central targets for drug discovery in academic and industrial research. Dysregulated kinases in diseases such as cancer have been addressed by a vast diversity of small molecule inhibitors, and a number of kinase inhibitors has been identified and approved by the FDA, including examples such as Erlotinib and Gefitinib.

The protein kinase B or Akt (PKB/Akt) is a serine/threonine kinase, which is activated in cells exposed to diverse stimuli such as hormones and growth factors. The protein kinase Akt features a regulatory pleckstrin homology (PH) domain, in addition to the catalytic kinase domain, allowing for membrane attachment upon growth factor stimulation and activation by phosphorylation via the upstream kinase phosphoinositide-dependent kinase-1 (PDK1). The activation mechanism of Akt remains to be fully characterised but occurs downstream of phosphoinositide 3-kinase (PI-3K). PI3K/Akt signaling mediates most of the cellular processes which comprise the hallmarks of cancer. Therefore, Akt dysregulation is directly associated with neoplastic transformation and malignant progression as well as increased resistance to chemo- and radiotherapy in a variety of solid tumors such as breast, prostate, and colorectal cancer. To this end, chemical modulation of dysregulated Aid using selective small molecule inhibitors provides a promising perspective for the treatment of patients suffering from diverse forms of cancer.

Therefore, the object underlying the present invention was to provide a compound that inhibits the Akt kinase.

The problem is solved by a 2,3-diphenyl-1,6-naphthyridine-5-one derivative according to general formula (I) as given as follows and/or racemates, enantiomers, stereoisomers, solvates, hydrates, and pharmaceutically acceptable salts and/or esters thereof:

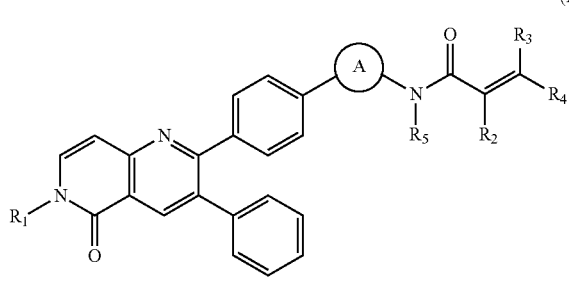

(I)

wherein:
A is a linker having a chain length of between 6 to 14 and comprises at least one 5- to 10-membered ring moiety;
$R_1$ is selected from the group comprising hydrogen, linear $C_1$-$C_5$-alkyl, branched $C_3$-$C_5$-alkyl and/or $C_3$-$C_7$-cyclo alkyl;
$R_2$, $R_3$, $R_4$ are selected, the same or independently of the other, from the group comprising hydrogen, CN, $CF_3$, linear $C_1$-$C_5$-alkyl, branched $C_3$-$C_5$-alkyl and/or $C_3$-$C_7$-cyclo alkyl, or
$R_2$ and $R_3$ form a triple bond between the carbon atoms to which they are attached;
$R_5$ is selected from the group comprising hydrogen, linear $C_1$-$C_5$-alkyl, branched $C_3$-$C_5$-alkyl and/or $C_3$-$C_7$-cyclo alkyl,
wherein the alkyl and cyclo alkyl groups of $R_1$, $R_2$, $R_3$, $R_4$, $R_5$ may comprise one or more heteroatoms selected from the group comprising O, N and/or S and/or be substituted by one or more halogen.

Surprisingly, it was found that 2,3-diphenyl-1,6-naphthyridine-5-one derivatives according to the invention bind with high potency and selectivity to the serine/threonine kinase Akt over other protein kinases with similar characteristics, and particularly exhibit isoform selectivity to Akt1 over Akt2 and Akt3. 2,3-Diphenyl-1,6-naphthyridine-5-one derivatives exhibited an excellent selectivity profile, exclusively targeting Akt isoforms without affecting kinases revealing high sequence and structural homology.

Using gastrointestinal stromal tumor cells, the selectivity of particular 2,3-diphenyl-1,6-naphthyridine-5-one derivatives for Akt1 in a cellular setting was demonstrated, whilst sparing further oncogenic protein kinases, such as c-KIT and Erk1/2. The 2,3-diphenyl-1,6-naphthyridine-5-one derivative further demonstrated to be a cell permeable effector of Akt in various cancer cell lines. These observations introduce the prospect of utilizing 2,3-diphenyl-1,6-naphthyridine-5-one derivatives for further medicinal chemistry approaches. 2,3-Diphenyl-1,6-naphthyridine-5-one derivatives particularly may contribute to the development of covalently modulating anticancer drugs.

The term "alkyl" according to the invention is to be understood as meaning straight-chain or branched alkyl groups. The term "linear $C_1$-$C_5$-alkyl" as used herein refers to straight-chain groups having 1 to 5 carbon atoms. Linear $C_1$-$C_5$-alkyl groups may be selected from the group comprising methyl, ethyl, n-propyl, n-butyl and n-pentyl. Preferred linear $C_1$-$C_5$-alkyl groups are selected from methyl and ethyl. A preferred branched "$C_3$-$C_5$-alkyl" is selected from isobutyl, tert.-butyl, sec.-butyl and/or isopentyl. A most preferred branched "$C_3$-$C_5$-alkyl" is isopropyl.

The term "$C_5$-$C_7$-cyclo alkyl" according to the invention is to be understood as meaning a 5- to 7-membered saturated ring. Preferred cycloalkyl groups are selected from the group comprising cyclopentyl and/or cyclohexyl.

The term "halogen" according to the invention is to be understood as meaning fluorine, chlorine, bromine or iodine, preferably fluorine, chlorine or bromine.

The 2,3-diphenyl-1,6-naphthyridine-5-one derivatives show excellent selectivity to Akt kinase and high potency. It is assumed that a covalent and allosteric inhibition of the Akt kinase is provided. The 2,3-diphenyl-1,6-naphthyridine-5-one structure is assumed to provide for allosteric interaction with the pleckstrin homology (PH) domain of the Akt kinase. The 2,3-diphenyl-1,6-naphthyridine-5-one structure advantageously showed a particular effective binding affinity. Tryptic digestion and mass spectrometric analysis of Akt kinase molecules treated with 2,3-diphenyl-1,6-naphthyridine-5-one derivatives further showed that two non-catalytic A-loop cysteines at positions 296 and 310 of Akt kinase (Cys296 and Cys310) are covalently modified by the 2,3-diphenyl-1,6-naphthyridine-5-one derivatives. It is assumed that this covalent interaction is provided by the part of the structure providing a reactive alkenyl or alkynyl group.

The parts of the 2,3-diphenyl-1,6-naphthyridine-5-one derivatives providing the covalent and the allosteric inhibition with Akt kinase are connected via the linker A. The linker A has a chain length of between 6 to 14 and comprises at least one 5- to 10-membered ring moiety.

The term "5- to 10-membered ring moiety" according to the invention refers to a stable 5- to 7-membered monocyclic ring or a 7- to 10-membered bicyclic ring which is either saturated or unsaturated, and which may comprise from 1 to 3 heteroatoms selected from the group comprising N, O and/or S and/or be substituted by one or more halogen, such as chlorine or fluorine. The term "5- to 10-membered ring moiety" includes bicyclic groups in which a 5- or 6-membered heterocyclic ring is fused to a benzene ring.

The 5- to 10-membered ring moiety may be selected from the group comprising benzene, furan, tetrahydrofuran, thiophene, tetrahydropyran, pyrrole, pyrrolidine, imidazole, 1,2,4-triazole, piperidine, piperazine, pyridine, pyrimidine, morpholine or azacycloheptane. Further preferred heterocycles are selected from the group comprising furan-2-yl, tetrahydrofuran-2-yl, tetrahydrofuran-3-yl, tetrahydropyran-2-yl, 1,3-dioxolan-5-yl, pyrrol-1-yl, pyrrol-2-yl, pyrrolidin-1-yl, isoxazol-3-yl, isoxazol-4-yl, 1,2-di-thiazolin-5-yl, imidazol-1-yl, 1,2,4-triazol-1-yl, 1,3,4-triazol-1-yl, thiophen-2-yl, piperidin-1-yl, piperidin-4-yl, pyridin-2-yl, pyridin-3-yl, pyridin-4-yl, pyrimidin-2-yl, pyrimidin-4-yl, pyrimidin-5-yl, morpholin-1-yl, azacycloheptan-1-yl and/or benzo-1,2,3-thiadiazol-7-yl.

The 5- to 10-membered ring moiety may be a saturated or unsaturated 6-membered ring. The 6-membered ring may comprise from 1 to 3 heteroatoms selected from the group comprising N, O and/or S and/or be substituted by one or more halogen, such as chlorine or fluorine. The 6-membered ring may be selected from benzene, piperidin-1-yl, piperidin-4-yl, piperrazin-1-yl and piperrazin-4-yl. The linker A may comprise two 6-membered rings. The linker A may comprise a 6-membered ring and a 5-membered ring or a 6-membered ring and a bicyclic group.

The ring moiety advantageously provides for the stability of the linker A. The linker A may comprise at least one ring moiety, or may comprise two or three ring moieties. The linker A connects the moieties of the molecule designed for covalent and the allosteric interaction with the Akt kinase. The linker A further provides a certain distance of the moieties to ensure proper and independent interaction with the kinase. A chain length of between 6 to 14 carbon or hetero atoms was shown to be effective. The chain length preferably may be in a range from 6 to 12, or in a range from 7 to 10, or in a range from 8 to 9 carbon or hetero atoms. It is to be understood that the 5- to 10-membered ring moiety will not add to the chain length of between 6 to 14 carbon or hetero atoms but is included in this chain length.

In preferred embodiments of the 2,3-diphenyl-1,6-naphthyridine-5-one derivative, A is selected from the group comprising the structural elements (A1) to (A12) as liven as follows:

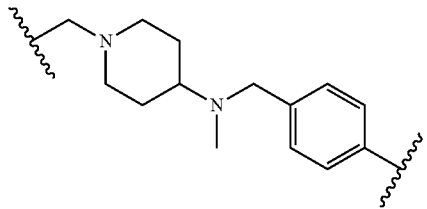

(A1)

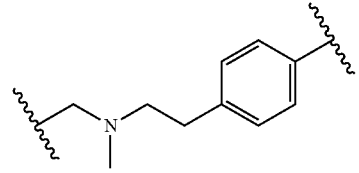

(A2)

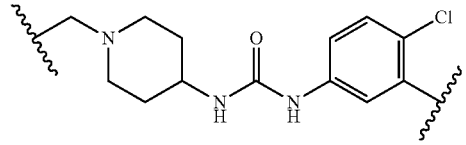

(A3)

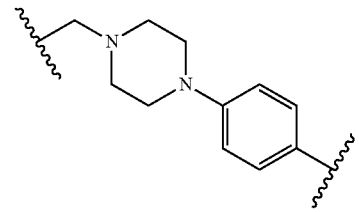

(A4)

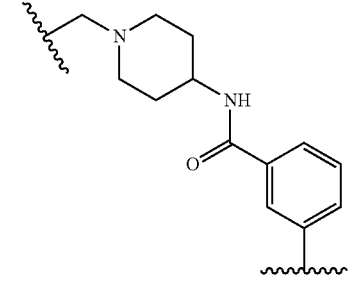

(A5)

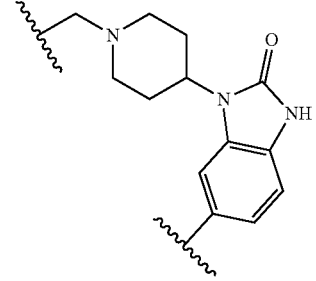

(A6)

-continued (A7)
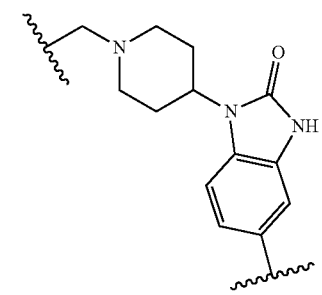

(A8)
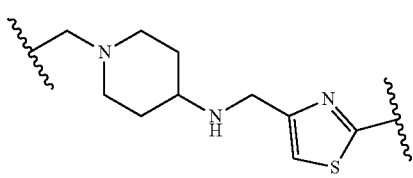

(A9)
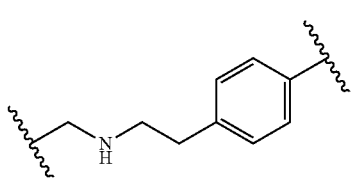

(A10)
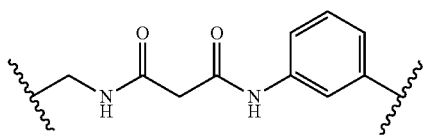

(A11)
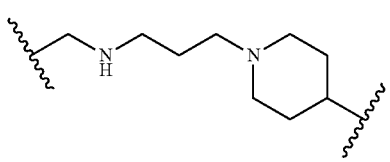

(A12)
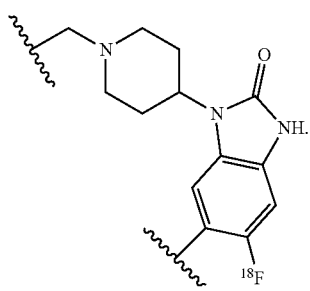

Unless specifically stated otherwise, compounds, groups or substituents denoted with Arabic numerals differ from compounds, groups or substituents denoted with Roman numerals or a combined naming of numerals and letters, that is, compounds, groups or substituents are different compounds, groups or substituents.

The 2,3-diphenyl-1,6-naphthyridine-5-one derivative comprises substituents $R_1$ to $R_5$. $R_1$ is selected from the group comprising hydrogen, linear $C_1$-$C_5$-alkyl, branched $C_3$-$C_5$-alkyl and/or $C_3$-$C_7$-cyclo alkyl, wherein the alkyl and cyclo alkyl groups may comprise one or more heteroatoms selected from the group comprising O, N and/or S and/or be substituted by one or more halogen. $R_1$ may be a 5- or 6-membered cyclo alkyl group. Preferably, $R_1$ is hydrogen or a linear $C_1$-$C_3$-alkyl group. More preferred, $R_1$ is hydrogen or methyl.

Also $R_5$ is selected from the group comprising hydrogen, linear $C_1$-$C_5$-alkyl, branched $C_3$-$C_5$-alkyl and/or $C_3$-$C_7$-cyclo alkyl, wherein the alkyl and cyclo alkyl groups may comprise one or more heteroatoms selected from the group comprising O, N and/or S and/or be substituted by one or more halogen. $R_5$ may be a 5- or 6-membered cyclo alkyl group. Preferably, $R_5$ is hydrogen or a linear $C_1$-$C_3$-alkyl group. More preferred, $R_5$ is hydrogen or methyl.

In a preferred embodiment of the 2,3-diphenyl-1,6-naphthyridine-5-one derivative, $R_1$ and $R_5$ are selected, the same or independently of the other, from the group comprising hydrogen and/or methyl. In most preferred embodiments, $R_1$ and $R_5$ are hydrogen.

The substituents $R_2$, $R_3$ and $R_4$ are selected, the same or independently of the other, from the group comprising hydrogen, CN, $CF_3$, linear $C_1$-$C_5$-alkyl, branched $C_3$-$C_5$-alkyl and/or $C_3$-$C_7$-cyclo alkyl, wherein the alkyl and cyclo alkyl groups may comprise one or more heteroatoms selected from the group comprising O, N and/or S and/or be substituted by one or more halogen. At least one or two of $R_2$, $R_3$ and $R_4$ may be CN or $CF_3$. $R_2$, $R_3$ and $R_4$ may be a linear $C_1$-$C_3$-alkyl group, preferably methyl or ethyl. One or more of $R_2$, $R_3$ and $R_4$ may be branched $C_3$-$C_5$-alkyl comprising at least one nitrogen atom, for example —(CH$_2$)—N(CH$_3$)$_2$. One or more of $R_2$, $R_3$ and $R_4$ may be branched $C_3$-$C_5$-alkyl substituted by one or more chlorine atoms. In preferred embodiments of the 2,3-diphenyl-1,6-naphthyridine-5-one derivative, $R_2$, $R_3$ and $R_4$ are hydrogen.

In alternative embodiments, $R_2$ and $R_3$ form a triple bond between the carbon atoms to which they are attached. This results in a triple bond between the carbon atoms.

In preferred embodiments, the 2,3-diphenyl-1,6-naphthyridine-5-one derivative is selected from the group of compounds comprising formulas (1a), (28), (29), (30), (31), (32) and/or (33) as indicated below and/or racemates, enantiomers, stereoisomers, solvates, hydrates, and pharmaceutically acceptable salts and/or esters thereof:

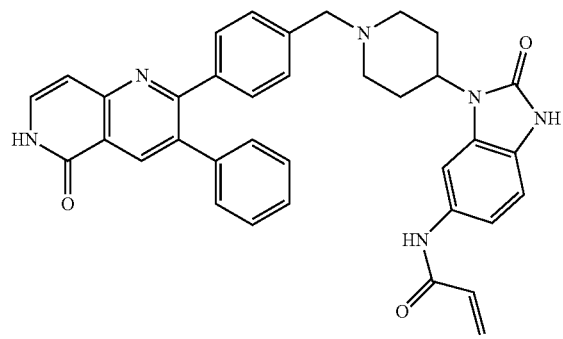
(1a)

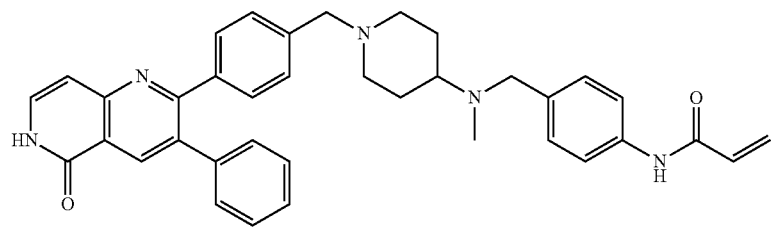
(28)

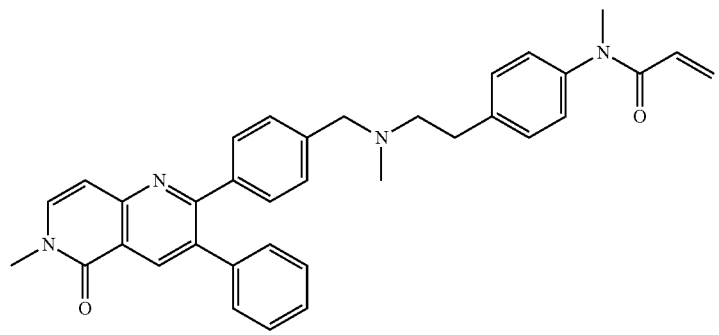
(29)

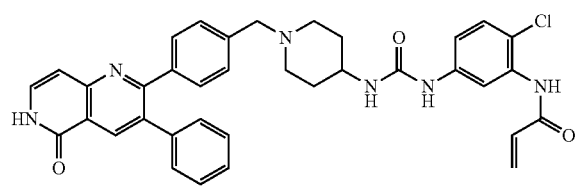
(30)

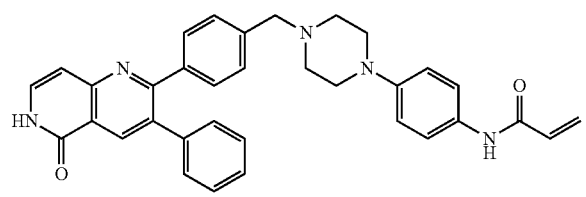
(31)

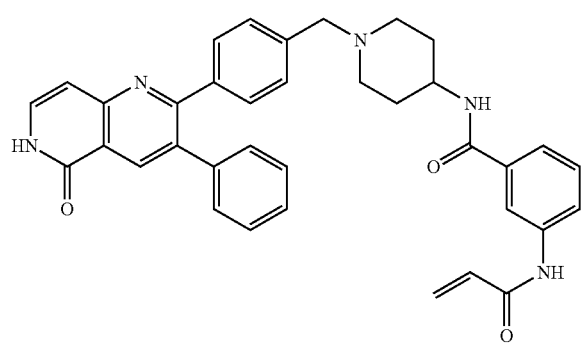
(32)

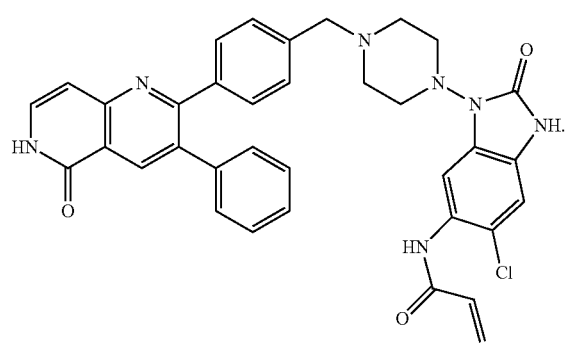
(33)

In especially preferred embodiments, the 2,3-diphenyl-1,6-naphthyridine-5-one derivative is selected from the group of compounds comprising formulas (1a), (30) and/or (32). These showed particular good half-maximal inhibitory concentrations and dissociation constants for the inhibition of Akt kinase. The most preferred 2,3-diphenyl-1,6-naphthyridine-5-one derivative is the compound according to formula (1a).

In further preferred embodiments, the 2,3-diphenyl-1,6-naphthyridine-5-one derivative is selected from the group of compounds comprising formulas (34), (35), (36), (37), (38), (39), (40) and/or (41) as indicated below and/or racemates, enantiomers, stereoisomers, solvates, hydrates, and pharmaceutically acceptable salts and/or esters thereof:

(34)
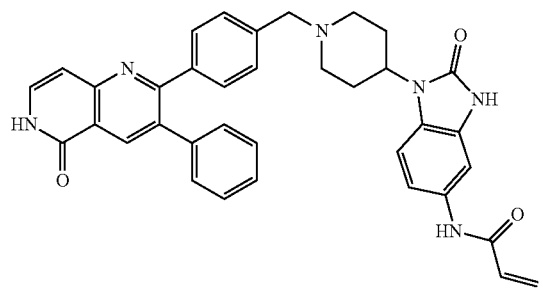

(35)
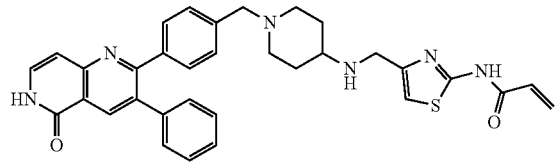

(36)
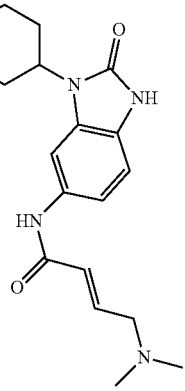

(37)
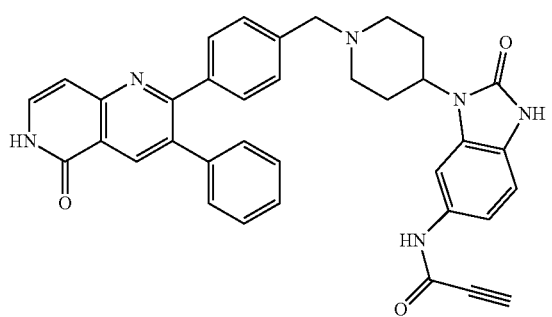

(38)
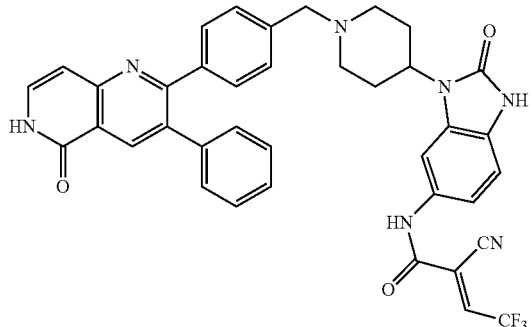

(39)
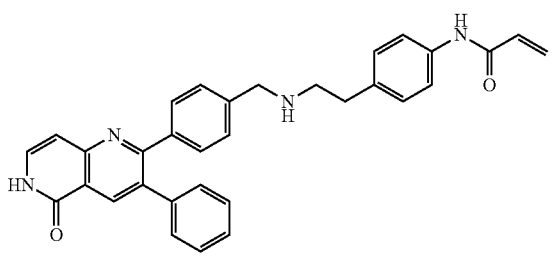

(40)
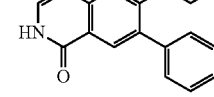

(41)

In embodiments, the 2,3-diphenyl-1,6-naphthyridine-5-one derivative comprises a fluorescent label or a radionuclide such as $^{18}F$. Fluorescent or radioactive labels are particularly suitable for a medical use.

Examples for 2,3-diphenyl-1,6-naphthyridine-5-one derivatives comprising a fluorescent label or a radionuclide are selected from the group comprising formulas (42), (43) and/or (44) as indicated below and/or racemates, enantiomers, stereoisomers, solvates, hydrates, and pharmaceutically acceptable salts and/or esters thereof:

(42)
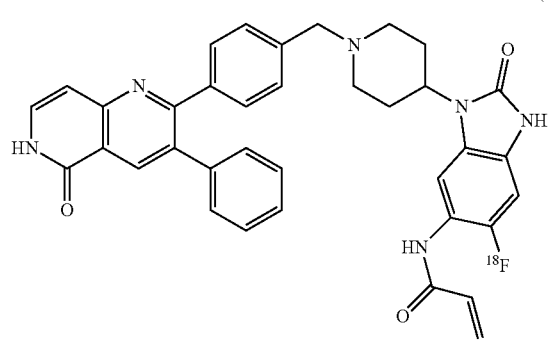

(43)
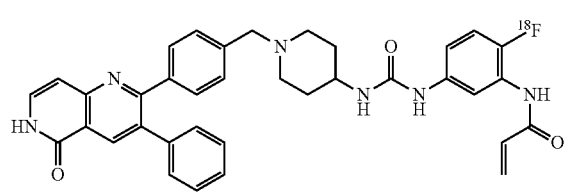

(44)
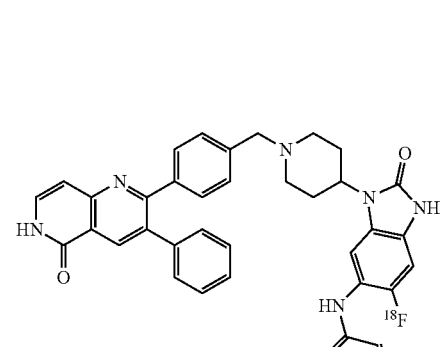
Fluorsecent Label.

In further preferred embodiments, the 2,3-diphenyl-1,6-naphthyridine-5-one derivative is selected from the group of compounds comprising formulas (45), (46), (47), (48), (49) and/or (50) as indicated below and/or racemates, enantiomers, stereoisomers, solvates, hydrates, and pharmaceutically acceptable salts and/or esters thereof:

(45)
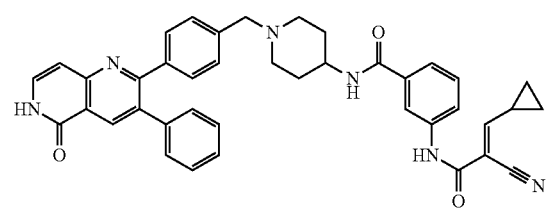

(46)
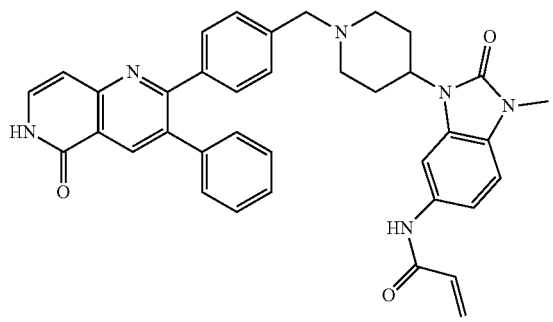

(47)
(48)
(49)
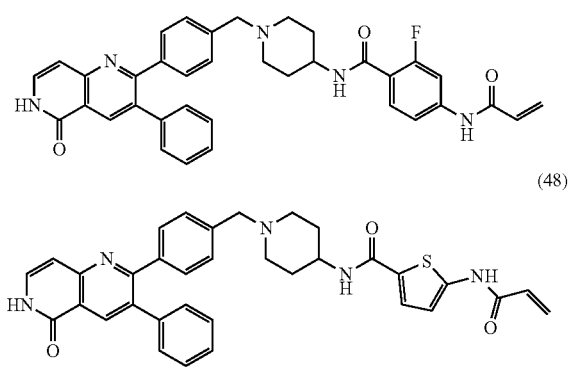

(50)

The 2,3-diphenyl-1,6-naphthyridine-5-one derivative is of formula (46) is particularly preferred.

The compounds described herein contain one or more asymmetric centres and may thus give rise to stereo isomers (configurational isomers). The present invention includes all such possible stereo isomers as well as their mixtures, and pharmaceutically acceptable salts thereof.

The 2,3-diphenyl-1,6-naphthyridine-5-one derivative according to the invention may be usable in the form of its solvates, hydrates, and pharmaceutically acceptable salts and esters.

The term "pharmaceutically acceptable salt" refers to salts prepared from pharmaceutically acceptable non-toxic bases or acids. A pharmaceutically acceptable salt can be conveniently prepared from pharmaceutically acceptable non-toxic bases, including inorganic bases and organic bases, organic anions, organic cations, halides or alkaline. The term pharmaceutically acceptable salt includes alkali metal salts and addition salts of free acids or free bases. Suitable pharmaceutically acceptable base addition salts include metallic salts and organic salts. Preferred salts derived from inorganic bases include ammonium, calcium, magnesium, potassium and sodium salts. Salts derived from pharmaceutically acceptable organic non-toxic bases include salts of primary, secondary, and tertiary amines. The 2,3-diphenyl-1,6-naphthyridine-5-one derivative may be used in the form of a hydrochloride or maleate.

A further aspect of the present invention relates to a 2,3-diphenyl-1,6-naphthyridine-5-one derivative according to the invention, for use as a medicament or a diagnostic reagent.

The 2,3-diphenyl-1,6-naphthyridine-5-one derivatives are potent covalent-allosteric inhibitors of the kinase Akt. The 2,3-diphenyl-1,6-naphthyridine-5-one derivatives combine an outstanding selectivity for the Akt kinase PH domain with the pharmacological and therapeutic benefits of being a targeted and irreversible modulator also binding covalently to Akt kinase, which includes superior drug-target residence time and increased potency. These features of the PH domain-dependent covalent-allosteric inhibitors allow to target Akt kinase for either therapeutic or diagnostic use. Akt signaling mediates most of the cellular processes which comprise the hallmarks of cancer.

A particular aspect of the present invention therefore relates to the 2,3-diphenyl-1,6-naphthyridine-5-one derivative according to the invention, for use in the diagnosis or treatment of cancer. The 2,3-diphenyl-1,6-naphthyridine-5-one derivatives are useful for a variety of cancer including leukemia (blood cancer), but particularly are for use for solid tumours. As used herein, the term "solid tumour" refers to a solid mass of cancer cells that grow in organ systems and can occur anywhere in the body. The term solid tumour as used herein does not refer to blood cancers. In embodiments, the solid tumours are selected from the group comprising breast cancer, prostate cancer, colorectal cancer, ovarian cancer, thyroid cancer, lung cancer, liver cancer, pancreatic cancer, gastric cancer, melanoma (skin cancer), lymphoma and glioma.

For use as a medicament or a diagnostic reagent the 2,3-diphenyl-1,6-naphthyridine-5-one derivatives can be used or included in a composition. A further aspect of the present invention relates to a diagnostic composition comprising a 2,3-diphenyl-1,6-naphthyridine-5-one derivative according to the invention. Such a diagnostic composition is particularly for use in the detection or diagnosis of cancer, particularly for use in the detection or diagnosis of solid tumours.

The 2,3-diphenyl-1,6-naphthyridine-5-one derivative will bind specifically to Akt kinase to mark a cancerous cell present in a sample. The 2,3-diphenyl-1,6-naphthyridine-5-one derivative can comprise a labelling which provides that the 2,3-diphenyl-1,6-naphthyridine-5-one derivative bound to Akt kinase can be detected by determining the presence or absence of a signal provided by the label. For example, the 2,3-diphenyl-1,6-naphthyridine-5-one derivative can be labelled with a fluorescent label such as a fluorescent dye. Fluorescence-labelling, for example provided by a fluorescence dye, can provide a visualisation of the 2,3-diphenyl-1,6-naphthyridine-5-one derivative by fluorescence or laser scanning microscopy or flow cytometry. Further, the 2,3-diphenyl-1,6-naphthyridine-5-one derivative can be labelled with a radioactive nuclide such as $^{18}F$ and detected by radiation dosimetry.

Besides being useful for detecting or diagnosing cancer by recognising Akt kinase in tumour cells, the 2,3-diphenyl-1,6-naphthyridine-5-one derivatives inhibits Akt kinase and thus also can be usable for therapy. Accordingly, in another aspect the present invention relates to a pharmaceutical composition comprising as an active ingredient a 2,3-diphenyl-1,6-naphthyridine-5-one derivative according to the invention. The pharmaceutical composition particularly is suitable for use in the treatment of cancer, particularly in the treatment of solid tumours.

The 2,3-diphenyl-1,6-naphthyridine-5-one derivative can be dissolved or dispersed in a pharmaceutically acceptable carrier. The term "pharmaceutical or pharmacologically acceptable" refers to molecular entities and compositions that do not produce an adverse, allergic or other untoward reaction when administered to a subject, such as, for example, a human, as appropriate. The pharmaceutical carrier can be, for example, a solid, liquid, or gas. Suitable carriers and adjuvants can be solid or liquid and correspond to the substances ordinarily employed in formulation technology for pharmaceutical formulations. For compositions convenient pharmaceutical media may be employed. For example, water, buffers, glycols, oils, alcohols and the like may be used to form liquid preparations such as solutions. The composition may comprise a pharmaceutical carrier, which can be, for example, a solid, liquid, or gas. Suitable carriers preferably are liquid and correspond to the substances ordinarily employed in formulation technology for pharmaceutical formulations. The compositions particularly the pharmaceutical composition may be produced under sterile conditions using standard pharmaceutical techniques well known to those skilled in the art.

The present invention also relates to the use of a 2,3-diphenyl-1,6-naphthyridine-5-one derivative according to the invention, for the manufacture of a medicament or a diagnostic reagent, particularly for the manufacture of a diagnostic reagent for the detection or diagnosis of cancer, or a medicament for the treatment of cancer, particularly solid tumours.

A further aspect of the present invention relates to a method of detecting or diagnosing cancer or a predisposition of cancer, the method comprising the step of detecting the binding of a 2,3-diphenyl-1,6-naphthyridine-5-one derivative according to the invention to Akt kinase, particularly Akt1, in a cell, tissue, or sample obtained from a subject.

As used herein, the term "sample" refers to any material, which probably contains tumour cells, including any liquid or fluid sample or solid material, particularly a sample derived from a biological source such as a patient or test subject. The term sample particularly refers to biological material, for example cells or tissues, biological fluids or supernatants. The biological material can be a tissue specimen removed from a cancer subject, preferably humans, for example, by surgical resection or biopsy. The biological material can be a body fluid such as blood, serum, plasma, saliva, phlegm and urine.

The method comprises bringing the 2,3-diphenyl-1,6-naphthyridine-5-one derivative according to the invention into contact with a sample, which probably contains tumour cells. The sample may be derived from a biological source such as a cancer subject. The sample for example can comprise cells or a tissue specimen isolated from a cancer subject, preferably a human, for example, by surgical resection or biopsy. The sample also can be a body fluid such as blood, serum, plasma, saliva, phlegm and urine. The method of detecting or diagnosing cancer in a sample by using the 2,3-diphenyl-1,6-naphthyridine-5-one derivative particularly is an in vitro or ex vivo method.

A further aspect of the present invention relates to a method of treating cancer, particularly solid tumours, the method comprising the step of administering to a subject a therapeutically effective amount of a 2,3-diphenyl-1,6-naphthyridine-5-one derivative according to the invention.

Subjects include both human subjects and animal subjects, particularly mammalian subjects such as human subjects or mice or rats for medical purposes. The term "therapeutically effective amount" is used herein to mean an amount or dose sufficient to cause an improvement in a clinically significant condition in the subject.

The cancer includes leukemia (blood cancer). Particularly cancer refers to solid tumours. Solid tumours may be selected from the group comprising breast cancer, prostate cancer, colorectal cancer, ovarian cancer, thyroid cancer, lung cancer, liver cancer, pancreatic cancer, gastric cancer, melanoma (skin cancer), lymphoma and glioma.

Unless otherwise defined, the technical and scientific terms used herein have the same meaning as commonly understood by one of ordinary skill in the art to which this invention belongs.

The examples which follow serve to illustrate the invention in more detail but do not constitute a limitation thereof.

The figures show:

FIG. 1 An overview of the synthesis of a 2,3-diphenyl-1,6-naphthyridine-5-one derivative according to an embodiment of the invention according to example 1 and of a compound for comparison according to example 2.

FIG. 2 An overview of the synthesis of a compound for comparison according to example 3. FIG. 2a shows the steps 3.2.1 to 3.2.8 and FIG. 2b shows step 3.2.9.

FIG. 3 iFLiK binding analysis of the compounds of examples 1 to 4, and controls. Representative results obtained from three independent measurements are shown and data depict the average±s.d. of quadruplicate measurements.

FIG. 4 Activity based screening of the compounds of examples 1 to 4. Representative results obtained from three independent measurements are shown and data depict the average±s.d. of quadruplicate measurements.

FIG. 5 shows the results of the time-dependent activity-based screening of the compounds of examples 1 (FIGS. 5a) and 2 (FIG. 5b) and MK-2206 (FIG. 5c). Data depict the average±s.d. of duplicate measurements.

FIG. 6 shows the $IC_{50}$ values plotted versus the incubation time for the compounds according to formulas (1a) (FIGS. 6a) and (2a) (FIG. 6b). Representative results obtained from three independent measurements are shown and the average±s.d. for $k_{inact}$, $K_i$ and $k_{inact}/K_i$ were calculated from triplicate measurements.

FIG. 7 shows the inhibition of a screening of a panel of 100 different protein kinases at a concentration of 1 µM of the 2,3-diphenyl-1,6-naphthyridine-5-one derivative of formula (1a). The depicted data show average % inhibition of two independent measurements for assessed kinases.

Figure 1:
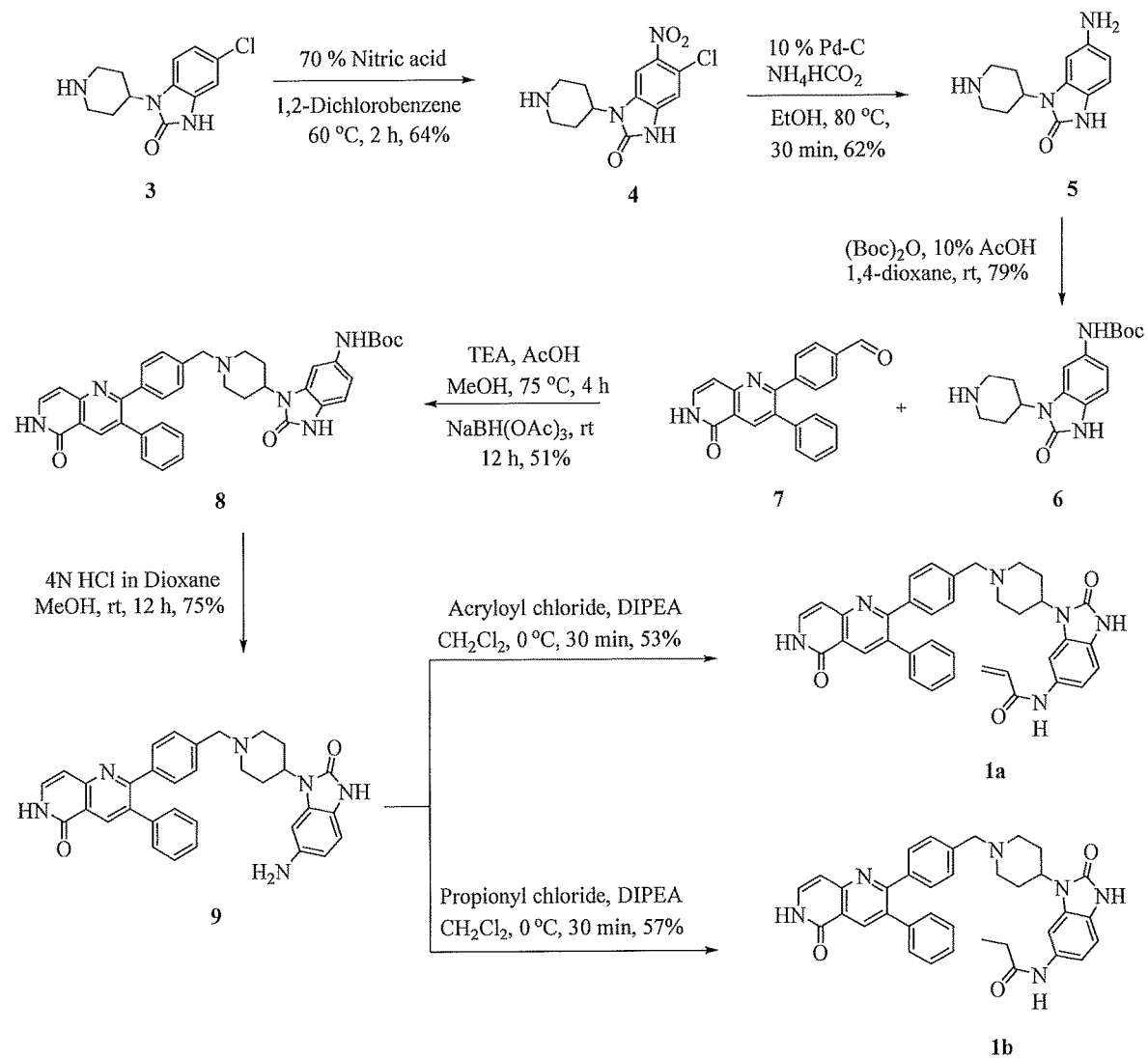

Chemicals were purchased from Acros, Fluka, Merck or Sigma-Aldrich and used without further purification, unless stated otherwise.

EXAMPLE 1

Synthesis of the Compound According to Formula (1a): N-(2-oxo-3-(1-(4-(5-oxo-3-phenyl-5,6-dihydro-1,6-naphthyridin-2-yl) benzyl) piperidin-4-yl)-2,3-dihydro-1H-benzo[d]imidazol-5-yl) acrylamide Step 1.1 Synthesis of 5-chloro-6-nitro-1-(piperidin-4-yl)-1,3-dihydro-2H-benzo[d]imidazol-2-one (4)

5-chloro-1-(piperidin-4-yl)-1,3-dihydro-2H-benzo[d]imidazol-2-one (3) (2 g, 8.0 mmol) was dissolved in 1,2-dichlorobenzene (40 mL) and 70% nitric acid (1 g, 16.0 mmol) was added drop wise to the above stirred solution at room temperature (RT, 20±2° C.). After being stirred for 2 h at 60° C. the reaction mixture was cooled down to RT. The precipitated crystals were separated by filtration and washed with diethyl ether (2×50 mL) and water. The crude product was recrystallized from hot ethanol and dried over high vacuum for 1 h which gives the title compound (4) as pale yellow solid (1.51 g, 64%).

Step 1.2 Synthesis of 6-amino-1-(piperidin-4-yl)-1,3-dihydro-2H-benzo[d]imidazol-2-one (5)

5-Chloro-1-(piperidin-4-yl)-1,3-dihydro-2H-benzo[d]imidazol-2-one (4) (2 g, 6.7 mmol) of step 1.1 and 10% Pd/C (0.2 g) was dissolved in ethanol (40 mL) and allowed to stir for 30 min at 80° C. Ammonium formate (4.0 g, 67 mmol) was added to the above stirred reaction mass at RT. After being stirred for 30 min at 80° C., reaction mixture was cooled to RT and filtered through a pad of celite. Excess solvent was removed and crude mass was purified by flash chromatography (5% MeOH/$CH_2Cl_2$) solvent system to afford the compound 6-amino-1-(piperidin-4-yl)-1,3-dihydro-2H-benzo[d]imidazol-2-one (5) as off white solid (0.97 g, 62%).

Step 1.3 Synthesis of tert-Butyl(2-oxo-3-(piperidin-4-yl)-2,3-dihydro-1H-benzo[d]imidazol-5-yl)carbamate (6)

$(Boc)_2O$ (0.88 mL, 3.8 mmol) in 1,4-dioxane (34.2 mL) was added drop wise to the stirred solution of 6-amino-1-(piperidin-4-yl)-1,3-dihydro-2H-benzo[d]imidazol-2-one (5) of step 1.2 (0.9 g, 3.8 mmol) in 10% AcOH (34.2 mL) and allowed to stir overnight at RT. The reaction mixture was washed with diethyl ether (2×25 mL) and aqueous solution was basified with 2N NaOH (5 mL) and extracted with $CH_2Cl_2$ (2×50 mL). Organic layer was washed with brine, dried over $Na_2SO_4$ and excess solvent was removed. The crude mass was purified by flash chromatography (4% MeOH/$CH_2Cl_2$) solvent system to afford the title compound tert-butyl (2-oxo-3-(piperidin-4-yl)-2,3-dihydro-1H-benzo[d]imidazol-5-yl)carbamate (6) as pale yellow liquid (1.05 g, 79%).

Step 1.4 Synthesis of 4-(5-oxo-3-phenyl-5,6-dihydro-1,6-naphthyridin-2-yl) benzaldehyde (7)

4-(5-oxo-3-phenyl-5,6-dihydro-1,6-naphthyridin-2-yl) benzaldehyde (7) was synthesized according to the procedure described in Z. Fang, J. R. Simard, D. Plenker, H. D. Nguyen, T. Phan, P. Wolle, S. Baumeister, D. Rauh, *ACS Chem. Biol.* 2015, 10, 279-288.

Step 1.5 Synthesis of tert-Butyl (2-oxo-3-(1-(4-(5-oxo-3-phenyl-5,6-dihydro-1,6-naphthyridin-2-yl) benzyl) piperidin-4-yl)-2,3-dihydro-1H-benzo[d]imidazol-5-yl) carbamate (8)

tert-butyl (2-oxo-3-(piperidin-4-yl)-2,3-dihydro-1H-benzo[d]imidazol-5-yl)carbamate (6) (0.5 g, 1.5 mmol) and 4-(5-oxo-3-phenyl-5,6-dihydro-1,6-naphthyridin-2-yl)benzaldehyde (7) of step 1.4 (0.49 g, 1.5 mmol) were dissolved in dry MeOH (20 mL), TEA (2 drops) and AcOH (2 drops) and allowed to stir for 4 h at 75° C. Then NaBH$_3$CN (0.31 g, 1.5 mmol) was added at RT and the reaction mass was allowed to stir overnight. The solvent was evaporated under reduced pressure and residue was purified by flash chromatography (2-4% of MeOH/CH$_2$Cl$_2$) to afford the title compound tert-butyl (2-oxo-3-(1-(4-(5-oxo-3-phenyl-5,6-dihydro-1,6-naphthyridin-2-yl)benzyl)piperidin-4-yl)-2,3-dihydro-1H-benzo[d]imidazol-5-yl)carbamate (8) as pale yellow liquid (0.46 g, 51%).

Step 1.6 Synthesis of 2-(4-((4-(6-amino-2-oxo-2,3-dihydro-1H-benzo[d]imidazol-1-yl) piperidin-1-yl) methyl) phenyl)-3-phenyl-1,6-naphthyridin-5(6H)-one (9)

Tert-butyl(2-oxo-3-(1-(4-(5-oxo-3-phenyl-5,6-dihydro-1,6-naphthyridin-2-yl)benzyl)piperidin-4-yl)-2,3-dihydro-1H-benzo[d]imidazol-5-yl)carbamate (8) of step 1.5 (200 mg, 0.31 mmol) was dissolved in ethyl acetate (25 mL) and 4N HCl in dioxane (5 mL) was added dropwise at 0° C. by means of an ice-bath and allowed to stir overnight at RT. The precipitate was filtered and washed with EtOAc (20 mL) and dissolved in water (20 mL). Aqueous layer was basified with sat NaHCO$_3$ and extracted with CH$_2$Cl$_2$, washed with brine and dried over Na$_2$SO$_4$. Excess solvent was removed and crude residue was purified by flash chromatography (7% MeOH/CH$_2$Cl$_2$) to obtain the title product 9 as pale yellow solid (120 mg, yield 75%).

Step 1.7 Synthesis of N-(2-oxo-3-(1-(4-(5-oxo-3-phenyl-5,6-dihydro-1,6-naphthyridin-2-yl) benzyl) piperidin-4-yl)-2,3-dihydro-1H-benzo[d]imidazol-5-yl) acrylamide (1a)

N,N-Diisopropylethylamine (DIPEA) (0.096 mL, 0.55 mmol) was added to the stirred solution of 2-(4-((4-(6-amino-2-oxo-2,3-dihydro-1H-benzo[d]imidazol-1-yl)piperidin-1-yl)methyl)phenyl)-3-phenyl-1,6-naphthyridin-5(6H)-one (9) of step 1.6 (0.06 g, 0.11 mmol) in CH$_2$Cl$_2$ (5 mL) at 0° C. by means of an ice-bath. Acryloyl chloride (0.084 mL, 0.11 mmol) was added dropwise to the above stirred reaction mixture at 0° C. and left to react at RT for 16 h. The reaction mixture was quenched with a saturated NaHCO$_3$ and the product was extracted with CH$_2$Cl$_2$ (3×20 mL). The combined organic layers were dried over MgSO$_4$ and filtered. The solvent was removed in vacuo to yield the crude product which was purified by flash chromatography (8% MeOH/CH$_2$Cl$_2$) to afford the title compound 1a (0.035 g, 53%) (R$_f$=0.35, 8% MeOH/CH$_2$Cl$_2$) as off white solid. An overview of the synthesis is shown in FIG. 1.

COMPARATIVE EXAMPLE 2 SYNTHESIS OF N-(2-OXO-3-(1-(4-(5-OXO-3-PHENYL-5,6-DIHYDRO-1,6-NAPHTHYRIDIN-2-YL)BENZYL) PIPERIDIN-4-YL)-2,3-DIHYDRO-1H-BENZO[D] IMIDAZOL-5-YL) PROPIONAMIDE (1b)

DIPEA (0.05 mL, 0.27 mmol) was added to the stirred solution of 2-(4-((4-(6-amino-2-oxo-2,3-dihydro-1H-benzo[d]imidazol-1-yl)piperidin-1-yl)methyl)phenyl)-3-phenyl-1,6-naphthyridin-5(6H)-one (9) of step 1.6 (0.03 g, 0.05 mmol) in CH$_2$Cl$_2$ (5 mL) at 0° C. by means of an ice-bath. Propionyl chloride (0.005 mL, 0.06 mmol) was added dropwise to the above stirred reaction mixture at 0° C. and left to react at RT for 16 h. The reaction mixture was quenched with a saturated NaHCO$_3$ and the product was extracted with CH$_2$Cl$_2$ (3×20 mL). The combined organic layers were dried over MgSO$_4$ and filtered. The solvent was removed in vacuo to yield the crude product which was purified by flash chromatography (8% MeOH/CH$_2$Cl$_2$) to afford the title compound 1b (0.019 g, 57.5%) (R$_f$=0.4, 8% MeOH/CH$_2$Cl$_2$) as off white solid.

COMPARATIVE EXAMPLE 3

Synthesis of the Compound According to Formula (2a)

Step 3.1.1 Synthesis of tert-Butyl 4-azidopiperidine-1-carboxylate (11)

A 50 mL two-neck round-bottomed flask was charged with DMSO (5 mL) and tert-butyl 4-bromopiperidine-1-carboxylate (10) (1.01 g, 3.82 mmol). This was followed by stirring at RT until the solution became clear and the starting material had dissolved. Sodium azide (1.2 equiv, 0.301 g, 4.64 mmol) was then added and the colorless reaction mixture was stirred at 60° C. for 18 h. The reaction mixture was diluted with distilled H$_2$O and the product was extracted with EtOAc (5×80 mL). The combined organic layers were then washed with brine, dried over MgSO$_4$ and filtered. The solvent was removed in vacuo to yield the crude product which was purified by CC (5% to 20% EtOAc/Hexane) to afford the title compound (11) (0.762 g, 3.37 mmol, 88%) (R$_f$=0.47, 10% EtOAc/Hexane) as a colorless oil.

Step 3.1.2 Synthesis of 4-Azidopiperidin-1-ium Chloride (12)

A one-neck round-bottomed flask was charged with tert-butyl 4-azidopiperidine-1-carboxylate 11 of step 3.1.1 (0.714 g, 3.16 mmol) and 4 M HCl in 1,4-dioxane (6 mL). The reaction mixture was stirred at RT for 23 h after which solvent was removed in vacuo to afford the crude title compound 12 (0.508 g, 3.12 mmol, 99%) as a pale yellow solid.

Step 3.1.3 Synthesis of N-(3-ethynylphenyl)acrylamide (14)

A Schlenk tube was charged with dichloromethane (DCM) (15 mL), 3-ethynylaniline 13 (0.20 mL, 0.22 g, 1.9 mmol) and triethanolamine (TEA) (4.5 equiv, 1.20 mL, 0.871 g, 8.61 mmol). The colorless reaction mixture was cooled to 0° C. by means of an ice-bath and acryloyl chloride (4.5 equiv, 0.70 mL, 0.78 g, 8.6 mmol) was added in a drop wise manner. The reaction mixture turned a milky yellow color over time. After addition of the acryloyl chloride, the reaction mixture was left to stir at RT for 18 h. The reaction was quenched with a saturated solution of aqueous $NaHCO_3$ and the product was extracted with DCM (3×150 mL). The combined organic layers were dried over $MgSO_4$ and filtered. The solvent was removed in vacuo to yield the crude product which was purified by CC (20% EtOAc/Hexane) to afford the title compound 14 (0.317 g, 1.85 mmol, 97%) ($R_f$=0.20, 20% EtOAc/Hexane) as a pale yellow solid.

Step 3.1.4 Synthesis of N-(3-Ethynylphenyl)propionamide (15)

A 50 mL two-neck round-bottomed flask was charged with DCM (50 mL), 3-ethynylaniline 13 (0.20 mL, 0.22 g, 1.9 mmol) and TEA (5.1 equiv, 1.35 mL, 0.890 g, 9.69 mmol). The colorless reaction mixture was cooled to 0° C. by means of an ice-bath and propionyl chloride (5.1 equiv, 0.85 mL, 0.91 g, 9.8 mmol) was added in a dropwise manner. The reaction mixture turned milky over time. After addition of the propionyl chloride, the reaction mixture was left to stir at RT for 17 h. The reaction was quenched with a saturated solution of aqueous $NaHCO_3$ and the product was extracted with DCM (4×50 mL). The combined organic layers were dried over $MgSO_4$ and filtered. The solvent was removed in vacuo to yield the crude product which was purified by CC (20% EtOAc/Hexane) to afford the title compound 15 (0.331 g, 1.91 mmol, quantitative) ($R_f$=0.69, 40% EtOAc/Hexane) as a pale yellow solid.

Step 3.2.1 Synthesis of 2-(4-Bromophenyl)imidazo[1,2-a]pyridine (18)

A 100 mL three-neck round-bottomed flask was charged with 2,4'-dibromoacetophenone 17 (6.08 g, 21.9 mmol), 2-aminopyridine 16 (1.1 equiv, 2.31 g, 24.5 mmol) and degassed acetone (45 mL). The reaction flask was fitted with a reflux condenser and the reaction mixture was heated at 80° C. for 3 h. Additional acetone (20 mL) was added during this time. The reaction mixture was subsequently allowed to cool to room temperature and transferred to a 250 mL one-neck round-bottomed flask. The solvent was removed in vacuo and HBr (45 mL) and MeOH (90 mL) was added to the reaction mixture. The reaction flask was again fitted with a reflux condenser and the reaction mixture was heated at 80° C. for 1 h. The reaction mixture was cooled to 0° C. by means of an ice-bath. The white precipitate was then filtered through a sinter funnel, washed with distilled $H_2O$ and dried under vacuum to afford the crude title compound 18 (5.69 g, 20.8 mmol, 95%) ($R_f$=0.36, 40% EtOAc/Hexane) as a white solid which was not further purified.

Step 3.2.2 Synthesis of 4-(Imidazo[1,2-a]pyridin-2-yl)benzonitrile (19)

A 10-20 mL microwave vial was charged with 2-(4-bromophenyl)imidazo[1,2-a]pyridine 18 of step 3.2.1 (1.01 g, 3.71 mmol), CuCN (1.5 equiv, 0.500 g, 5.58 mmol) and degassed DMF (12 mL). The vial was placed in the microwave reactor and heated at 160° C. for 30 min to dissolve the reagents. It was then heated at 200° C. for 4 h. The reaction mixture was allowed to cool to RT and diluted with ethylenediamine (5 mL) and $H_2O$ (20 mL). Extraction was done with DCM (10×50 mL) and the combined organic layers were dried over anhydrous $MgSO_4$ and filtered. The solvent was removed in vacuo and the dark brown crude material was purified by CC (50% EtOAc/Hexane with 1% TEA) to afford the still impure title compound 19 (0.786 g). It was then further purified by a second round of CC (50% EtOAc/Hexane with 1% TEA) to afford the title compound 19 (0.498 g, 2.27 mmol, 61%) ($R_f$=0.32, 40% EtOAc/Hexane) as a pale yellow solid.

Step 3.2.3 Synthesis of 4-(3-Bromoimidazo[1,2-a]pyridin-2-yl)benzonitrile (20)

A 50 mL one-neck round-bottomed flask was charged with 4-(imidazo[1,2-a]pyridin-2-yl)benzonitrile 19 of step 3.2.2 (0.203 g, 0.925 mmol) and MeCN (2 mL). NBS (2.0 equiv, 0.330 g, 1.85 mmol) was dissolved in MeCN (5 mL) and added to the reaction flask in three portions. A precipitate formed during the addition of the NBS and the reaction mixture was stirred at RT for 10 min and the solvent was removed in vacuo to yield a yellow solid which was diluted with saturated aqueous $NaHCO_3$ and extracted with DCM (4×50 mL). The combined organic layers were dried over $MgSO_4$ and filtered and the solvent was removed in vacuo. The yellow crude material was purified by CC (30% EtOAc/Hexane) to afford the still impure title compound 20 (0.312 g). It was then further purified by a second round of CC (30% EtOAc/Hexane) to afford the title compound 20 (0.181 g, 0.608 mmol, 66%) ($R_f$=0.47, 40% EtOAc/Hexane) as an off-white solid.

Step 3.2.4 Synthesis of 4-(3-Phenylimidazo[1,2-a]pyridin-2-yl)benzonitrile (22)

As described in S. Marhadour, M.-A. Bazin, P. Marchand, Tetrahedron Lett. 2012, 53, 297-300, a Schlenk tube was charged with 4-(3-bromoimidazo[1,2-a]pyridin-2-yl)benzonitrile 20 of step 3.2.3 (0.314 g, 1.05 mmol), phenylboronic acid 21 (1.2 equiv, 0.159 g, 1.30 mmol), $K_2CO_3$ (2.4 equiv, 0.356 g, 2.57 mmol) and $Pd(PPh_3)_4$ (5 mol %, 0.063 g, 0.54 mmol) and then evacuated and backfilled with $N_2$. Degassed 1,4-dioxane (2 mL) and $H_2O$ (1 mL) was added and it was again evacuated and backfilled with $N_2$. The reaction mixture was heated at 110° C. for 2.5 h and then allowed to cool to room temperature. The clear yellow reaction mixture was diluted with $H_2O$ (75 mL) and extracted with DCM (6×75 mL). The combined organic layers were dried over $MgSO_4$ and filtered and the solvent was removed in vacuo. The crude material was purified by CC (20% EtOAc/Hexane) to afford the title compound 22 (0.245 g, 0.830 mmol, 79%) ($R_f$=0.41, 40% EtOAc/Hexane) as an off-white solid.

Step 3.2.5 Synthesis of 4-(3-Phenylimidazo[1,2-a]pyridin-2-yl)benzaldehyde (23)

A 50 mL two-neck round-bottomed flask was charged with 4-(3-phenylimidazo[1,2-a]pyridin-2-yl)benzonitrile 22 of step 3.2.4 (0.261 g, 0.883 mmol), formic acid (6.5 mL) and Raney nickel (RaNi). The reaction mixture was heated at 90° C. for 28 h. It was then allowed to cool to RT, then filtered through cotton wool and diluted with saturated aqueous $NaHCO_3$ (200 mL). Extraction was done with EtOAc (5×75 mL) and the combined organic layers were dried over $MgSO_4$, filtered and the solvent was removed in vacuo. The yellow crude material was purified by CC (20% to 40% EtOAc/Hexane) to afford the title compound 23 (0.172 g, 0.577 mmol, 65%) ($R_f$=0.32, 40% EtOAc/Hexane) as a thick yellow oil/solid.

Step 3.2.6 Synthesis of [4-(3-Phenylimidazo[1,2-a]pyridin-2-yl)phenyl]methanol (24)

A 50 mL one-neck round-bottomed flask was charged with 4-(3-phenylimidazo[1,2-a]pyridin-2-yl)benzaldehyde 23 of step 3.2.5 (0.170 g, 0.569 mmol) and MeOH (3.5 mL). The milky yellow reaction mixture was cooled to 0° C. by means of an ice-bath and the sodium borohydride (2.1 equiv, 0.045 g, 2.30 mmol) was added. The resulting clear yellow reaction mixture was left to stir at 0° C. temperature for 30 min. The reaction was allowed to cool to RT and the solvent was removed in vacuo to yield a pale yellow oil to which distilled $H_2O$ was added. Extraction was done using EtOAc (4×150 mL) and the combined organic layers were dried over $MgSO_4$ and filtered. The solvent was removed in vacuo to yield the crude product which was purified by CC (40% to 50% to 80% EtOAc/Hexane) to afford the title compound 24 (0.135 g, 0.449 mmol, 79%) ($R_f$=0.11, 50% EtOAc/Hexane) as a white solid.

Step 3.2.7 Synthesis of 2-[4-(Chloromethyl)phenyl]-3-phenylimidazo[1,2-a]pyridine (25)

A 50 mL two-neck round-bottomed flask was charged with [4-(3-phenylimidazo[1,2-a]pyridin-2-yl)phenyl]methanol 24 of step 3.2.6 (0.121 g, 0.403 mmol) and DMF (5 mL). Carbon tetrachloride (2.5 mL) and triphenylphosphine (2.1 equiv, 0.223 g, 0.850 mmol) was added to the reaction mixture and the reaction flask was fitted with a reflux condenser. It was subsequently heated at 90° C. for 21 h. Additional triphenylphosphine (2.0 equiv, 0.216 g, 0.823 mmol) was then added to the reaction mixture and it was heated at 90° C. for an additional 5 h. The reaction mixture was diluted with distilled $H_2O$ and the product was extracted with EtOAc (3×150 mL). The combined organic layers were then dried over $MgSO_4$ and filtered and the solvent was removed in vacuo to yield the crude product which was purified by CC (30% EtOAc/Hexane) to afford the title compound 25 (0.149 g, still impure) ($R_f$=0.40, 40% EtOAc/Hexane) as a yellow oil.

Step 3.2.8 Synthesis of 2-{4-[(4-Azidopiperidin-1-yl)methyl]phenyl}-3-phenylimidazo[1,2-a]pyridine (26)

A 50 mL two-neck round-bottomed flask was charged with 4-azidopiperidin-1-ium chloride 12 (1.7 equiv, 0.114 g, 0.702 mmol), DMF (1 mL) and TEA (1.8 equiv, 0.10 mL, 0.073 g, 0.72 mmol). These were stirred together at RT and then 2-[4-(chloromethyl)phenyl]-3-phenylimidazo[1,2-a]pyridine 25 of step 3.2.7 (0.128 g, 0.403 mmol) dissolved in DMF (2 mL) was added. The reaction mixture was heated at 60° C. for 2.5 h. The reaction mixture was allowed to cool to RT and diluted with distilled $H_2O$. The product was extracted with EtOAc (3×150 mL) and the combined organic layers were then dried over $MgSO_4$ and filtered. The solvent was removed in vacuo to afford the crude product which was diluted with brine and extracted with diethyl ether and then purified by CC (80% EtOAc/Hexane) to afford the title compound 26 (0.115 g, 0.282 mmol, 70% over 2 steps) ($R_f$=0.12, 80% EtOAc/Hexane) as a thick yellow oil.

Step 3.2.9 Synthesis of N-[3-(1-{1-[4-(3-Phenylimidazo[1,2-a]pyridin-2-yl)benzyl]piperidin-4-yl}-1H-1,2,3-triazol-4-yl)phenyl]acrylamide (2a)

A Schlenk tube was charged with 2-{4-[(4-azidopiperidin-1-yl)methyl]phenyl}-3-phenylimidazo[1,2-a]pyridine 26 of step 3.2.8 (0.038 g, 0.094 mmol), N-(3-ethynylphenyl)acrylamide 14 of step 3.1.3 (2.2 equiv, 0.035 g, 0.20 mmol), N,N-diisopropylethylamine (3.1 equiv, 0.050 mL, 0.037 g, 0.29 mmol) and MeCN (1.5 mL). The milky yellow reaction mixture was heated to 25° C. to dissolve the contents and the reaction mixture turned an almost clear yellow. CuI (28 mol %, 5 mg, 0.03 mmol) was added and the reaction was stirred at 25° C. for 15 h. The reaction mixture was diluted with DCM, filtered through a cotton wool plug and concentrated in vacuo. The resulting orange crude material was purified by CC (1% to 2.5% MeOH/DCM) to afford the title compound 2a (0.068 g, quantitative) ($R_f$=0.19, EtOAc) as a pale yellow solid.

Figure 2A:
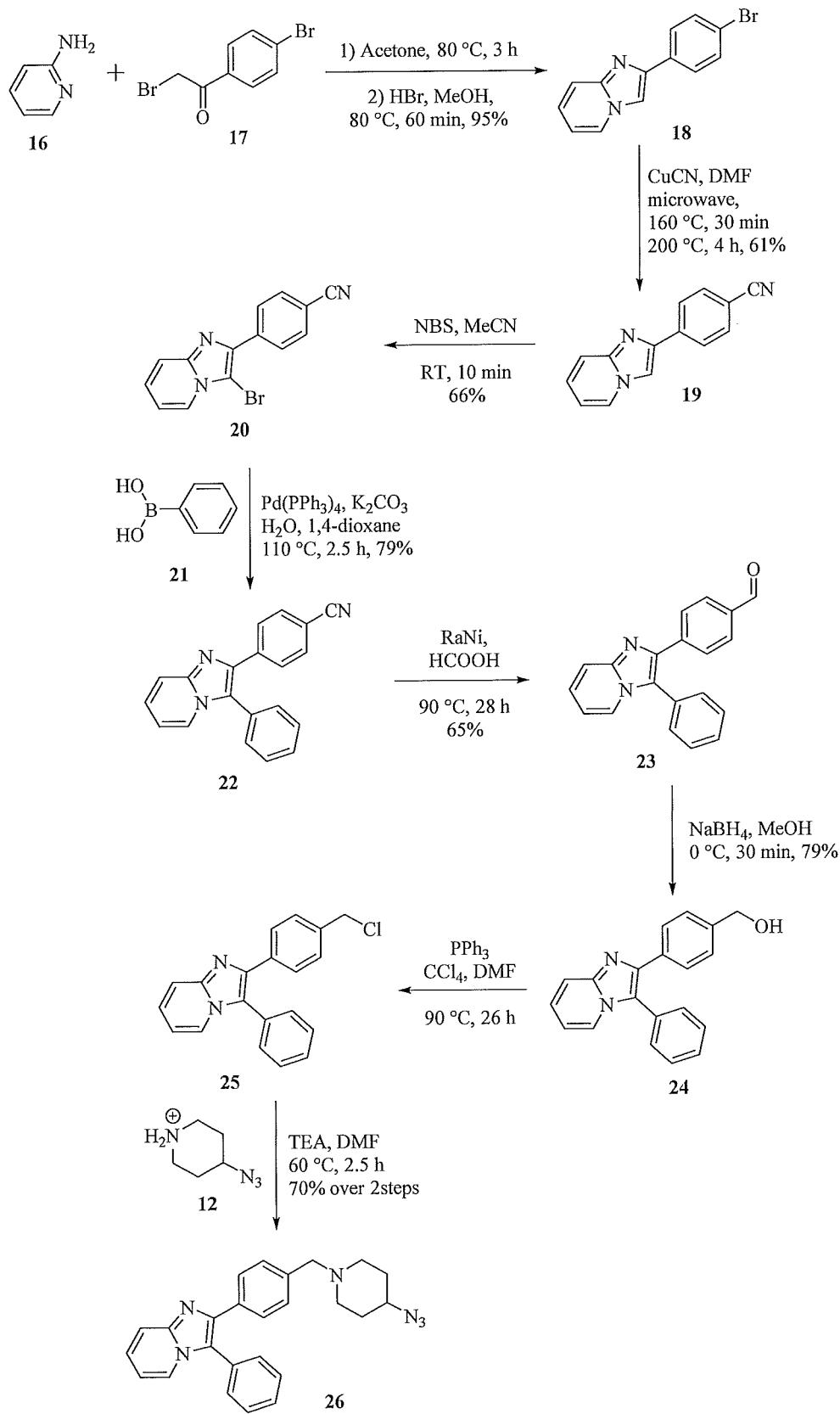
Figure 2B:
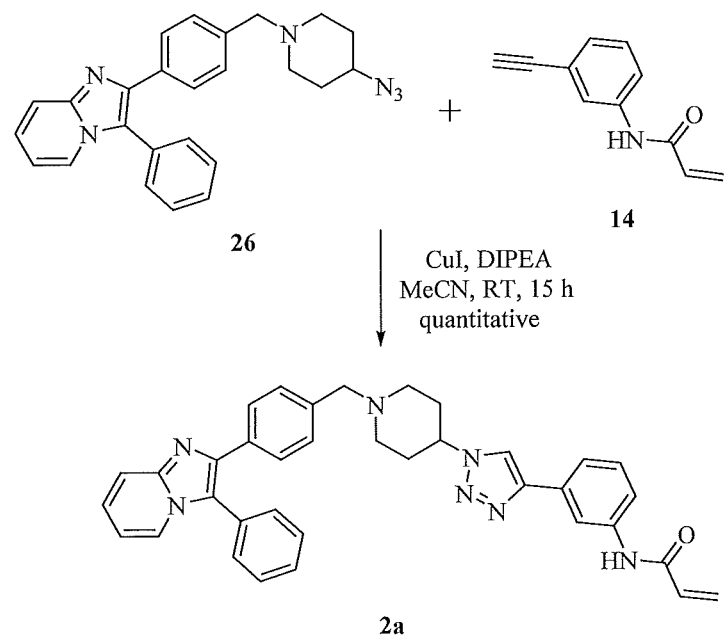

For characterization, ethyl acetate (EtOAc) and diethyl ether was visible in the $^1$H NMR spectrum, causing the excess mass of the product. It was trapped by the compound which was originally an oil before further drying under vacuum. The sample sent for biochemical evaluation was spread open for a high surface area to volume ratio and further dried under vacuum, ensuring a completely dry sample. A 2D NOESY spectrum was obtained to confirm synthesis of the required 1,4-disubstituted 1,2,3-triazole and not the 1,5-disubstituted 1,2,3-triazole. This NMR spectrum showed correlation between the triazole proton and the piperidinyl protons, confirming successful synthesis of the 1,4-disubstituted 1,2,3-triazole. The triazole proton in the 1,5-disubstituted 1,2,3-triazole would be too far from the piperidinyl protons to correlate. An overview of the synthesis is shown in FIGS. 2a and 2b.

COMPARATIVE EXAMPLE 4

Synthesis of N-[3-(1-{1-[4-(3-Phenylimidazo[1,2-a]pyridin-2-yl)benzyl]piperidin-4-yl}-1H-1,2,3-triazol-4-yl)phenyl]propionamide (2b)

A 25 mL one-neck round-bottomed flask was charged with 2-{4-[(4-azidopiperidin-1-yl)methyl]phenyl}-3-phenylimidazo[1,2-a]pyridine 26 of step 3.2.8 (0.038 g, 0.094 mmol), N-(3-ethynylphenyl)propionamide 15 of step 3.1.4 (2.0 equiv, 0.033 g, 0.19 mmol) and CuI (28 mol %, 5 mg, 0.03 mmol). MeCN (1.5 mL) and N,N-diisopropylethylamine (3.1 equiv, 0.050 mL, 0.037 g, 0.29 mmol) was subsequently added and the milky yellow reaction mixture was stirred at 25° C. for 21 h. The reaction mixture was diluted with DCM, filtered through a cotton wool plug and concentrated in vacuo. The resulting orange crude material was purified by CC (0.5% MeOH/EtOAc) to afford the still impure title compound 2b which was then further purified by a second round of CC (0.5% MeOH/EtOAc) to afford the title compound 2b (16 mg, 0.028 mmol, 29%) ($R_f$=0.073, 0.5% MeOH/EtOAc) as a pale yellow semi-solid.

Methods

Plasmid Construction:

The genes encoding for $His_6$-tagged full-length wild-type (wt) Akt1 and mutant full-length Akt1 (E49C, C296S, C310S, C344S) were generated synthetically (GeneArt, Regensburg, Germany). Afterwards they were cloned into pREN4427-HIS-DEST vector and introduced into a baculovirus using the BacMagic Kit (Calbiochem) in Sf9 cells (Invitrogen). Protein expression, purification and labeling was performed according to standard protocols.

Biochemical Assays:

iFLiK and HTRF studies were carried out as described in Z. Fang, J. R. Simard, D. Plenker, H. D. Nguyen, T. Phan, P. Wolle, S. Baumeister, D. Rauh, *ACS Chem. Biol.* 2015, 10, 279-288.

All reagents for HTRF experiments were purchased from Cisbio Bioassays, France. OriginPro 9.1G software (Origin-Lab Corporation, Northhampton, Mass.) was used for data analysis and data was fit to a sigmoidal dose-response model using the following four-parameter logistic equation:

$$y = A_2 + \frac{(A_2 - A_1)}{\left(1 + \left(\frac{x}{IC_{50}}\right)^p\right)} \quad (1)$$

($A_1$: bottom asymptote; $A_2$: top asymptote; $IC_{50}$: half-maximal inhibitory concentration; p: Hill coefficient)

Kinetic Characterization of Covalent Probe Compounds:

Time-dependent $IC_{50}$ measurements were performed with activated full-length Akt1 as described under "Biochemical assays". Briefly, $IC_{50}$ values were determined for twelve different incubation times and afterwards plotted versus accordingly. Data was analyzed according to literature procedure as described in B. F. Krippendorff, R. Neuhaus, P. Lienau, A. Reichel, W. Huisinga, J. Biomol. Screen. 2009, 14, 913-923. $K_i$ and $k_{inact}$ were calculated with XLfit (Version 5.4.0.8, IDBS, Munich, Germany) defining the substrate concentration as 250 nM and the corresponding substrate $K_M$ as 150 nM.

Mass Spectrometry:

Purified full-length wtAkt1 was thawed under cold water and diluted to a final concentration of 1 mg/mL in storage buffer (50 mM HEPES, 200 mM NaCl, 10% Glycerol, pH 7.4). 20 µL of the respective mixture were mixed with 2 molar equivalents of the compounds of formulas (1a) and (2a), respectively (10 mM in DMSO); samples containing equal volumes of DMSO were individually prepared for control measurements. Following incubation for thirty minutes on ice, the samples were analyzed by ESI-MS using an Agilent 1100 Series HPLC System connected to a ThermoFinnigan LTQ Linear Ion Trap mass spectrometer. Therefore, 6 µL of sample were injected and separated using a Vydac 214TP C4 5 u column (150 mm×2.1 mm) starting at 20% of solvent B for five minutes followed by a gradient up to 90% of solvent B over 14 min (flow rate 210 µL/min) with 0.1% TFA in water as solvent A and 0.1% TFA in acetonitrile as solvent B. After washing the column for two minutes with 90% of solvent B, the concentration of solvent A was increased to 80% in 1 min and the column was washed for five additional minutes. During the complete experiment, a mass range of 700 to 2000 m/z was scanned and raw data was deconvoluted and analyzed with MagTran and mMass (Version 5.5.0) software.

For ESI-MS/MS measurements, samples were denatured, separated via SDS-PAGE followed by staining with Coomassie Brilliant Blue and prepared according to standard tryptic in-gel digest protocols as described in A. Shevchenko, H. Tomas, J. Havlis, J. V. Olsen, M. Mann, Nat. Protoc. 2006, 1, 2856-2860. Subsequently, samples were thawed, dissolved in 20 µL of 0.1% TFA in water, sonicated at room temperature for 15 min, and centrifuged at 15000×g for 1 min shortly before analysis. 3 µL of sample were loaded onto a pre-column cartridge and desalted for 5 min using 0.1% TFA in water as eluent at a flow rate of 30 µL/min. The samples were back-flushed from the pre-column to the nano-HPLC column during the whole analysis. Elution was performed using a gradient starting at 5% B with a final composition of 30% B after 35 min (flow rate 300 nL/min) using 0.1% formic acid in water as eluent A and 0.1% formic acid in acetonitrile as eluent B and a column temperature of 40° C. The nano-HPLC column was washed by increasing the percentage of solvent B to 60% in 5 min and to 95% in additional 5 min, washing the columns for further 5 min, flushing back to starting conditions and equilibration of the system for 14 min. During the complete gradient cycle, a typical TOP10 shot-gun proteomics method for the MS and MS/MS analysis was used. For full scan MS experiments a mass range of m/z 300 to 1650 was scanned with a resolution of 70000. MS/MS experiments were followed by up to ten high energy collision dissociation (HCD) MS/MS scans with a resolution of 17500 of the most intense at least doubly charged ions. Data evaluation was performed using MaxQuant as decribed in Cox, M. Mann, Nat. Biotechnol. 2008, 26, 1367-1372. Spectra were searched against the Akt1-sequence and a contamination database using a false discovery rate of 1% on peptide and protein level using a decoy database for determination of the false discovery rate. For database search oxidation of methionine and N-terminal acetylation of proteins, carbamidomethylation of cysteines, and artificial modification of cysteines were defined as variable modifications.

Cell Culture:

GIST-T1 was established by Takahiro Taguchi (Kochi University, Kochi, Japan) from a human, untreated, metastatic GIST containing a 57 bp deletion in KIT exon 11 as described in H. Nakatani, M. Kobayashi, T. Jin, T. Taguchi, T. Sugimoto, T. Nakano, S. Hamada, K. Araki, Cancer Sci. 2005, 96, 116-119 and were cultured in DMEM high glucose media (Life Technologies, Germany), supplemented with 10% FBS (Biochrom, Berlin, Germany), 1% penicillin/streptomycin (PenStrep), and 1% L-Glutamine, in a humidified incubator at 37° C. and 5% $CO_2$.

Human ductal breast carcinoma cells (BT474) and human prostate adenocarcinoma cells (PC-3) were purchased from the ATCC (Bethesda, Md., USA) and were cultured in RPMI 1640 medium (Life Technologies, Germany) supplemented with 10% (v/v) fetal calf serum (FCS; Biochrom, Berlin, Germany) and maintained in a humidified incubator at 37° C. and 5% $CO_2$ (C200, Labotect Incubator, Göttingen, Germany).

Western Blotting:

For GIST-T1 cells protein lysates were prepared from cell line monolayers according to standard protocols as described in A. Duensing, F. Medeiros, B. McConarty, N. E. Joseph, D. Panigrahy, S. Singer, C. D. Fletcher, G. D. Demetri, J. A. Fletcher, *Oncogene* 2004, 23, 3999-4006. Protein concentrations were determined with the Bio-Rad Protein Assay (Bio-Rad Laboratories, Hercules, Calif.). Electrophoresis and immunoblotting were carried out as described in B. P. Rubin, S. Singer, C. Tsao, A. Duensing, M. L. Lux, R. Ruiz, M. K. Hibbard, C. J. Chen, S. Xiao, D. A. Tuveson, G. D. Demetri, C. D. Fletcher, J. A. Fletcher, *Cancer Res.* 2001, 61, 8118-8121. Changes in protein expression and phosphorylation as visualized by chemiluminescence were captured and quantified using a FUJI LAS3000 system with Science Lab 2001 ImageGauge 4.0 software (Fujifilm Medial Systems, Stamford Conn., USA).

BT474 and PC-3 cells were lysed for 10 min at 95° C. in 62.5 mM Tris-HCl (pH 6.8), 2% (w/v) SDS, 10% (v/v) glycerol, 80 mM DTT, and 0.01% (w/v) bromophenol blue (350.000 cells per 100 µL lysis buffer). Proteins were separated by SDS-PAGE and blotted onto PVDF-membranes (Roth, Karlsruhe, Germany) using Fastblot according to manufacturer's manual (B44, Biometra, Goettingen, Germany). After blocking with 5% (w/v) nonfat dry milk membranes were incubated at 4° C. over night with the respective primary antibody (1:20.000 for β-actin, 1:1000 for all other antibodies). After washing, the membranes were incubated for 1 h at room temperature with the secondary antibody (anti-IgG-HRP 1:2000, CST, Frankfurt, Germany) washed again and monitored by chemiluminescence imaging using FUSION Solo (peqlab, Erlangen, Germany) and appropriate ECL Prime Western blotting detection reagent according to the manufacturer's protocol (GE Healthcare/Amersham-Biosciences, Freiburg, Germany).

Antibodies:

Rabbit antibodies specific for Akt, phospho-Akt (Thr308 & Ser473), GSK-3β, phospho-GSK-3β (Ser9), p42/44 mitogen-activated protein kinase (MAPK), phospho-p44/42 MAPK (Thr202/Tyr204), S6 ribosomal protein, phospho-S6 ribosomal protein (Ser235/236), 4E-BP1, phospho-4E-BP1 (Ser65), as well as HRP-conjugated anti-rabbit and anti-mouse secondary antibodies were purchased from Cell Signaling (Frankfurt, Germany; Beverly, Mass.). Mouse anti-β-actin antibodies were obtained from Sigma-Aldrich (Deisenhofen, Germany; St. Louis, Mo.). Rabbit polyclonal antibodies for KIT and phospho-KIT (Tyr703) were from DAKO (Carpinteria, Calif.) and Cell Signaling (Beverly, Mass.), respectively.

EXAMPLE 5: KINETIC ANALYSIS OF AKT KINASE INHIBITION USING THE INTERFACE FLUORESCENT LABELS IN KINASES (iFLiK) SYSTEM

The compounds according to formulas (1a), (1b), (2a) and (2b) were subjected to kinetic analyses using the interface Fluorescent Labels in Kinases (iFLiK) system in order to determine the dissociation rates with respect to fluorescently labeled full-length Akt1. The iFLiK studies were carried out as described under "biochemical assays" using concentrations in a range of 0.1 nM to 12.5 µM. Further to the compounds of formulas (1a), (1b), (2a) and (2b), the known allosteric Akt inhibitor MK-2206 (Selleckchem) and ATP-competetive inhibitor GSK690693 (Selleckchem) were used for comparison. The final concentration of fluorophore-labeled recombinant Akt1 was 200 nM.

Figure 3:
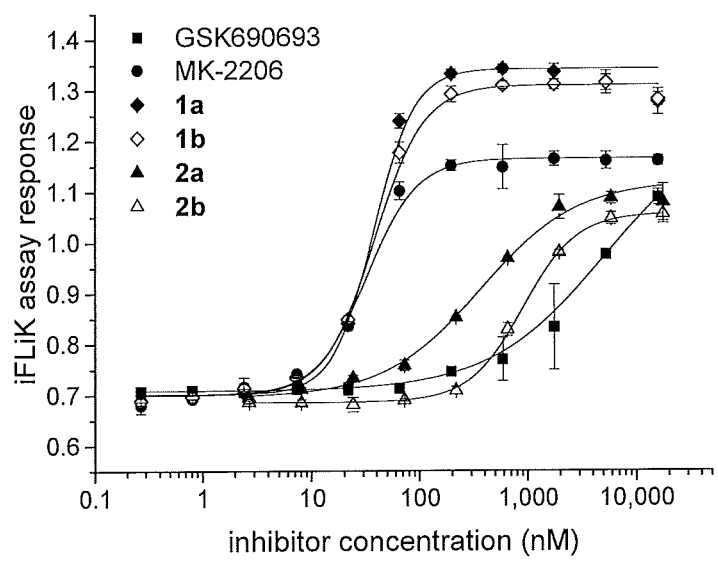

FIG. 3 shows the results of the binding analysis of the compounds. As can be taken from FIG. 3, the compounds according to formulas (1a) and (2a) exhibited similar binding characteristics as MK-2206. The compound of formula (2a), however, exhibited lower affinity to fluorescently labeled Akt1 compared to the compound of formula (1a). The compounds according to formulas (1b) and (2b), in turn, bound with comparable affinity to mutated full-length Akt1.

The following Table 1 shows the half-maximal inhibitory concentrations ($IC_{50}$) and dissociation constants ($K_d$) of the compounds according to formulas (1a), (1b), (2a) and (2b) and for the Akt inhibitors MK-2206 and GSK690693:

TABLE 1

| half-maximal inhibitory concentrations ($IC_{50}$), and dissociation constants ($K_d$): | | |
|---|---|---|
| Compound | $IC_{50}$/nM | $K_d$/nM |
| 1a | 0.2 ± 0.1 | 58 ± 8 |
| 1b | 7.5 ± 2 | 62 ± 12 |
| 2a | 372 ± 48 | 795 ± 176 |
| 2b | 992 ± 328 | 797 ± 180 |
| MK-2206 | 6.5 ± 0.8 | 69 ± 13 |
| GSK690693 | 2.3 ± 0.3 | n.r. | n.r. = no response up to 100 µM

The results indicated similar binding affinities for the 2,3-diphenyl-1,6-naphthyridine-5-one derivative according to formula (1a) of the invention and reference inhibitor MK-2206 (58±8 nM and 69±13 nM, respectively). The compound according to formula (2a) exhibited a significantly lower binding affinity for Akt1 (795±176 nM). The counterparts according to formulas (1b) and (2b), however, possessed comparable $K_d$ values (62±12 nM and 797±180 nM, respectively). These results were consistent with the fact that the full-length Akt protein used in these studies had been mutated for site specific fluorophore labeling by replacing all solvent-exposed cysteines with serines, including both A-loop cysteines, thereby preventing covalent bond formation.

These results show that the 2,3-diphenyl-1,6-naphthyridine-5-one derivatives show much better half-maximal inhibitory concentrations ($IC_{50}$) and dissociation constants ($K_d$) than the compounds of formulas (2a) and (2b) of Comparative Examples 3 and 4 having an imidazo-1,2-pyridine core.

The 2,3-diphenyl-1,6-naphthyridine-5-one derivatives according to formulas (28), (29), (30), (31), (32) and (33) were also subjected to kinetic analyses using the iFLiK system. The compound of formula (27) has a structure given as follows:

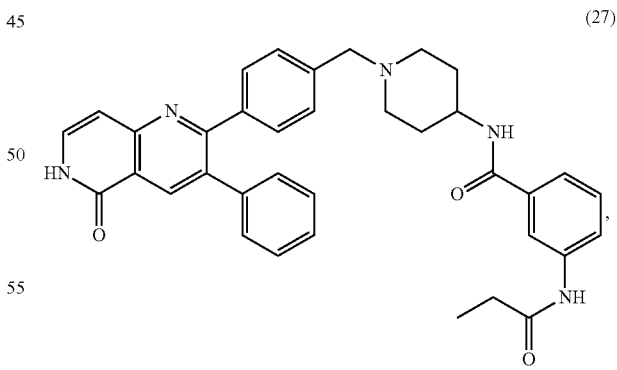

(27)

which compares to the compound of formula (32), but which has no alkenyl group and can therefore not form a covalent bond with Akt.

The following Table 2 shows the half-maximal inhibitory concentrations ($IC_{50}$) and dissociation constants ($K_d$) of the 2,3-diphenyl-1,6-naphthyridine-5-one derivatives according to formulas (28), (29), (30), (31), (32) and (33):

TABLE 2 half-maximal inhibitory concentrations (IC$_{50}$), and dissociation constants (K$_d$):

| Compound | K$_d$/nM | IC$_{50}$/nM |
|---|---|---|
| 28 | 1847 ± 521 | 147.1 ± 21.7 |
| 29 | 498 ± 140 | 249.2 ± 65.4 |
| 30 | 468 ± 53 | 6.0 ± 1.5 |
| 31 | 488 ± 117 | 190.3 ± 51.5 |
| 32 | 216 ± 173 | 2.7 ± 2.1 |
| 27 | 79 ± 21 | 18.2 ± 13.3 |
| 33 | 89 ± 5 | not determined |

These results show that also the 2,3-diphenyl-1,6-naphthyridine-5-one derivatives according to formulas (28), (29), (30), (31), (32) and (33) are useful inhibitors of Akt, and particularly the 2,3-diphenyl-1,6-naphthyridine-5-one derivatives of formulas (30) and (32) showed good half-maximal inhibitory concentrations (IC$_{50}$), and dissociation constants (K$_d$).

EXAMPLE 6: KINETIC ANALYSIS USING ACTIVITY-BASED STUDIES

The potential influence of the reactive alkenyl group functioning as a Michael acceptor was further evaluated and the inhibitory potencies further assessed in activity-based studies utilizing activated full-length wtAkt1 (Millipore). As in Example 5, the 2,3-diphenyl-1,6-naphthyridine-5-one derivative of formula (1a) and the compounds of formulas (1b), (2a) and (2b) and the known allosteric Akt inhibitor MK-2206 and ATP-competitive inhibitor GSK690693 were used for comparison. Concentrations in a range of 0.001 nM to 12.5 µM were used. The final concentration of recombinant Akt1 was 120 pM.

Figure 4:
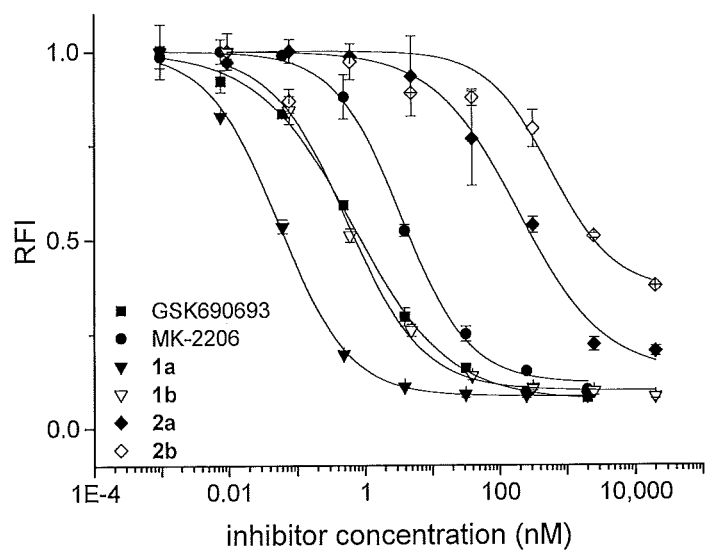

The FIG. 4 shows the results of the activity-based screening. As can be taken from the FIG. 4, the compounds of formulas (1a) and (2a) comprising an alkenyl group exhibited higher inhibitory potencies against full-length wtAkt1 compared to their counterparts (1b) and (2b), respectively. Notably, 2,3-diphenyl-1,6-naphthyridine-5-one derivative of formula (1a) inhibited Akt1 more potently than reference inhibitors GSK690693 (ATP-competitive inhibitor) and MK-2206 (allosteric, PH domain-dependent inhibitor). Whilst the compound of formula (2a) moderately inhibited Akt kinase activity in comparison to reference inhibitors MK-2206 and GSK690693 (372±48 nM vs. 7±1 nM and 2±1 nM, respectively), the 2,3-diphenyl-1,6-naphthyridine-5-one derivative according to formula (1a) exhibited a subnanomolar half-maximal inhibitory concentration (0.2±0.1 nM). In contrast, 10-fold and 4-fold higher concentrations of the compounds of formulas (1b) and (2b), respectively, were required to provoke half-maximum inhibition of Akt1. This suggests a covalent modification of Akt by the 2,3-diphenyl-1,6-naphthyridine-5-one derivative according to formula (1a) and compounds of formula (2a) as reason for their higher potency.

EXAMPLE 7: TIME-DEPENDENT ACTIVITY-BASED SCREENING

The compound according to formula (1a) in concentrations in a range of 1×10$^{-4}$ nM to 12.5 µM and the compound according to formula (1b) and the allosteric Akt inhibitor MK-2206 in concentrations in a range of 1×10$^{-3}$ nM to 12.5 µM were incubated with activated full-length wtAkt1 over 10, 30, 60 or 300 minutes, respectively, whereas durations of enzymatic and stop reactions were kept constant. The final concentration of recombinant Akt1 was 120 pM.

FIG. 5 shows the results of the time-dependent activity-based screening. As can be taken from FIG. 5a, the compound of formula (1a) exhibits time-dependent dose-response curves indicating a covalent mode of action. No differences were observed for MK-2206 and the compound of formula (1b), as shown in FIGS. 5b and 5c, respectively, therefore indicating reversible binding mechanisms as well as dynamic equilibrium binding.

These time-dependent IC$_{50}$ determinations further indicated a covalent mode of action for the 2,3-diphenyl-1,6-naphthyridine-5-one derivative according to formula (1a).

EXAMPLE 8: KINETIC CHARACTERIZATION BY DETERMINATION OF k$_{inact}$/K$_i$

The compounds according to formulas (1a) and (2a) were incubated with activated full-length wtAkt1 (Millipore) over a time period in a range of 1 minute to 120 minutes whereas durations of enzymatic and stop reactions were kept constant. Calculated IC$_{50}$ values were plotted versus the incubation time and data was fit as described in the literature to determine k$_{inact}$ and K$_i$ as described above.

The FIG. 6 shows the IC$_{50}$ values plotted versus the incubation time for the compounds according to formulas (1a) in FIGS. 6a and (2a) in FIG. 6b. Representative results obtained from three independent measurements are shown and the average±s.d. for k$_{inact}$, K$_i$ and k$_{inact}$/K$_i$ were calculated from triplicate measurements. k$_{inact}$/K$_i$ was calculated to 3.29±0.40 µM$^{-1}$ s$^{-1}$ for the 2,3-diphenyl-1,6-naphthyridine-5-one derivative of formula (1a) and to 0.0023±0.0003 µM$^{-1}$ s$^{-1}$ for the compound according to formula (2a).

The kinetic characterization of the compounds by determination of k$_{inact}$/K$_i$ indicated a significantly enhanced inhibition profile for the compound of formula (1a) compared to the compound of formula (2a), with respect to both affinity and covalent complex formation.

EXAMPLE 9: DETERMINATION OF BINDING PROPERTIES TO AKT1 USING ESI-MS

ESI-MS was used to investigate the respective binding properties to Akt1 as described under "Mass spectrometry". Mass spectrometry results showed that the treatment of recombinant wild-type Akt1 with the compounds according to the formulas (1a) and (2a) resulted in mass increases equivalent to the corresponding single labeled Akt1 of 587 and 572 Da, respectively, as compared to control Akt1 treated with DMSO. These results further substantiate the anticipated covalent binding mode correlating with the observed trends in activity-based studies.

EXAMPLE 10: DETERMINATION OF BINDING PROPERTIES TO AKT1 USING ESI-MS/MS ANALYSIS

The binding to Akt1 was further determined using ESI-MS/MS analysis after a tryptic digest of Akt treated with the compounds according to the formulas (1a) and (2a) as described under "Mass spectrometry".

Full-length wtAkt1 was expressed in Sf9 insect cells and purified with an ÄKTA pure FPLC system. Purified protein was incubated with a 2-fold molar excess of the compounds according to the formulas (1a) and (2a), respectively, and digested with trypsin after SDS-PAGE following standard protocols. Peptide fragments containing Cys296 and Cys310 modified by both the compounds according to the formulas (1a) and (2a) were identified with a sequence coverage >90%. This supports that the compounds according to the formulas (1a) and (2a) covalently bind to Akt1 at Cys296 and Cys310.

The kinetic analyses show that the 2,3-diphenyl-1,6-naphthyridine-5-one derivatives according to the invention provide promising biochemical inhibitory potency against Akt kinase. Further, mass spectrometry showed that the 2,3-diphenyl-1,6-naphthyridine-5-one derivative according to formula (1a) acts as an allosteric inhibitor of Akt kinase that moreover covalently modifies Akt at Cys296 and Cys310. It is assumed that the alkenyl group hence stabilizes an enzymatically inactive conformation of full length Akt.

EXAMPLE 11: DETERMINATION OF THE SELECTIVITY OF THE 2,3-DIPHENYL-1,6-NAPHTHYRIDINE-5-ONE DERIVATIVE OF FORMULA (1a) TO AKT KINASE

For the 2,3-diphenyl-1,6-naphthyridine-5-one derivative of formula (1a) according to the invention the selectivity for Akt1 over other protein kinases with similar characteristics was investigated focusing on a) members of the AGC kinase family, b) kinases featuring a PH domain and/or c) kinases containing cysteines on the activation loop. One hundred different protein kinases matching these criteria were assessed.

The 2,3-diphenyl-1,6-naphthyridine-5-one derivative of formula (1a) was screened against the panel of 100 different protein kinases at a compound concentration of 1 µM. Measurements were performed in duplicates and at the particular apparent ATP $K_M$ of each individual kinase employing the activity based Z'LYTE® kinase assay of the SelectScreen® Kinase Profiling Services (LifeTechnologies). The FIG. 7 shows the table of the profiling data. The depicted data show average % inhibition of two independent measurements for assessed kinases.

As can be taken from the FIG. 7, within the panel of kinases, solely the Akt isoforms 1,2 and 3 were significantly addressed with 98%, 96%, and 83% inhibition, respectively, at a concentration of 1 µM of the 2,3-diphenyl-1,6-naphthyridine-5-one derivative of formula (1a). The remaining 97 kinases were inhibited by less than 40%, the kinase MAP4K5 ranking fourth with 37% inhibition.

In conclusion, the compound of the invention exhibited an excellent selectivity profile, exclusively targeting Akt isoforms without affecting kinases revealing high sequence and structural homology.

EXAMPLE 12: DETERMINATION OF AKT INHIBITION IN CANCER CELLS

The inhibition of Akt kinase by the 2,3-diphenyl-1,6-naphthyridine-5-one derivative of formula (1a) was further investigated in cellular studies using prostate cancer (PC3), breast cancer (BT474), and gastrointestinal stromal tumor (GIST-T1) cell lines.

These cell lines possess genetic lesions (PC3: PTEN−/−, BT474: PI3K mut, HER2+; GIST T1: c-KIT mut) in the PI3K/Akt pathway and display differences in basal phospho-Akt levels. These cell lines were employed as model systems for Western Blot analyses to investigate both the cell penetrating effect of the 2,3-diphenyl-1,6-naphthyridine-5-one derivative of formula (1a) as well as its influence on cellular Akt1 and downstream GSK3β phosphorylation states. Cell culture, Western Blotting were performed as described above.

The prostate cancer (PC3) and breast cancer (BT474) cells were incubated for 24 hours with concentrations of 0.01 µM, 0.1 µM, 01 µM, and 10 µM of the compound of formula (1a) and MK-2206 as reference compound, respectively. Controls were treated with dimethyl sulfoxide (DMSO).

Figure 8:
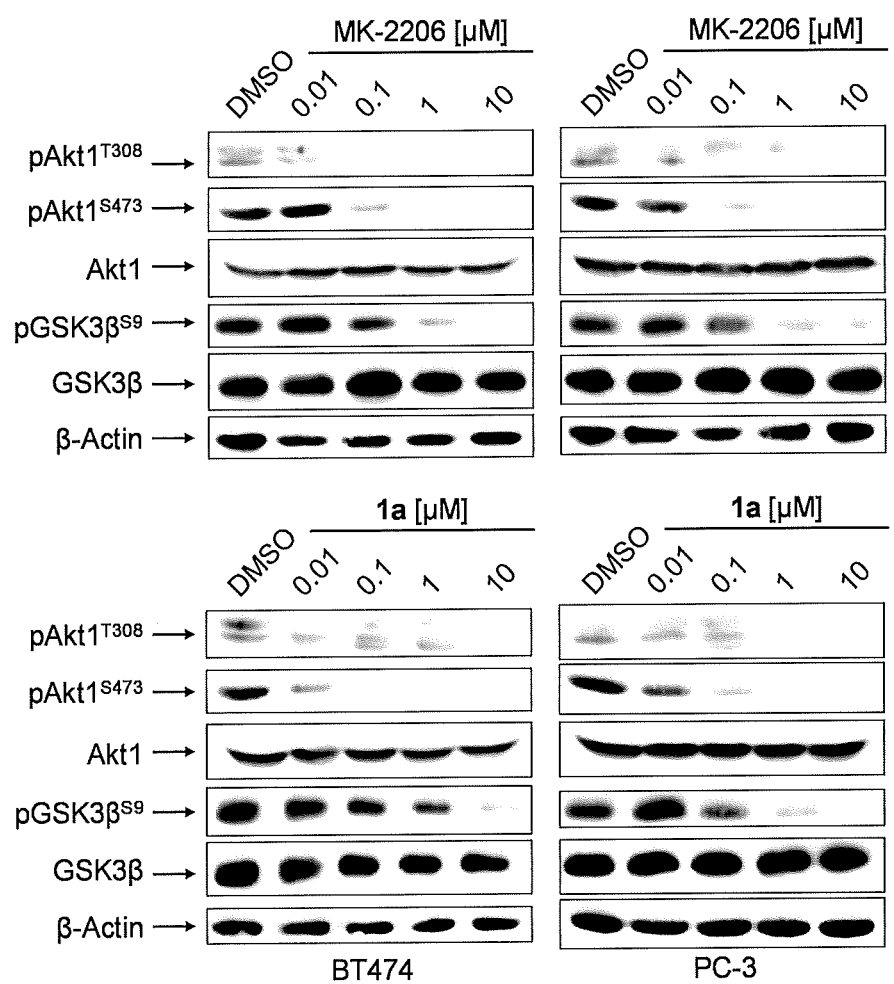
FIG. 8 shows Western blots of Akt1 and phosphorylated Akt1, and GSK3β and phosphorylated GSK3β upon treatment of breast cancer (BT474) and prostate cancer (PC-3) cells with different concentrations of the 2,3-diphenyl-1,6-naphthyridine-5-one derivative of formula (1a) and the Akt inhibitor MK 2206. β-Actin was used as loading control.

FIG. 8 shows the resulting Western blots of Akt1 and phosphorylated Akt1, and GSK3β and phosphorylated GSK3β in prostate cancer (PC3) and breast cancer (BT474) cells. β-Actin was used as loading control. As can be taken from FIG. 8, the Western blots show a sensitive dose-dependent decreases of pAkt1 at both Thr308 and Ser473 in PC3 and BT474 cancer cell lines. The results illustrate that the covalent-allosteric inhibitor of formula (1a) triggers dephosphorylation of Akt1 in a dose-dependent manner in breast cancer (BT474) and prostate cancer (PC-3) cells without affecting expression levels of Akt1. These results were correlated with decreased phosphorylation of the Akt1 substrate GSK3β upon treatment with the compound of formula (1a) analogous to clinical candidate MK 2206.

The gastrointestinal stromal tumor cells (GIST-T1) cells were incubated for 24 hours with concentrations of 0.001 µM, 0.005 µM, 0.01 µM, 0.05 µM, and 0.1 µM of the compound of formula (1a), respectively. 1 µM MK-2206, 1 µM GSK690693, and 0.1 µM Imatinib were used as reference compounds. Controls were treated with dimethyl sulfoxide (DMSO).

Figure 9:
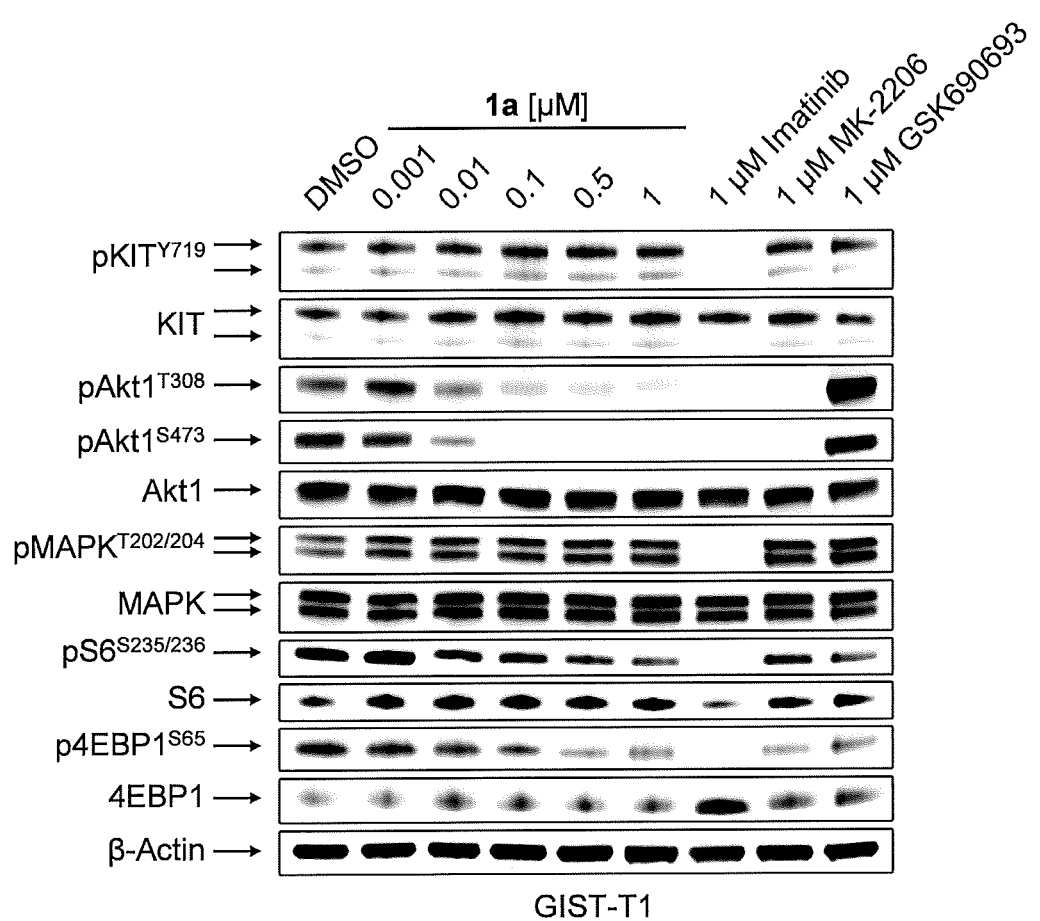
FIG. 9 shows Western blots of kinases upon treatment of gastrointestinal stromal tumor cells (GIST-T1) with different concentrations of the 2,3-diphenyl-1,6-naphthyridine-5-one derivative of formula (1a), the Akt inhibitors MK 2206 and GSK690693 and Imatinib. β-Actin was used as loading control.

FIG. 9 shows the resulting Western blots of the determined kinases in KIT-dependent GIST-T1 cells. Gastrointestinal stromal tumor cells (GIST-T1) exhibit high basal pAkt1 levels related to constitutively active KIT. Imatinib was used as positive control for KIT inhibition. As can be taken from the FIG. 9, treatment with the compound of formula (1a) reduces cellular pAkt1 levels at low nanomolar concentrations correlating with decreasing phosphorylation of downstream targets S6 and 4EBP1. The phosphorylation of other relevant protein kinases c-KIT and MAPK (Erk1/2) was not affected by treatment with the compound of formula (1a). Two bands are visible for KIT representing the mature glycosylated form and the immature form. Regarding MAPK, the bands relate to Erk1 and Erk2.

The Western blots demonstrate the compound of formula (1a) impairs Akt1 phosphorylation in cancer cells. Moreover, using KIT-dependent GIST-T1 cells, the results demonstrate the selectivity of the compound of formula (1a) for Akt1 in a cellular setting, whilst sparing further oncogenic protein kinases, such as c-KIT and Erk1/2.

The results in prostate cancer, breast cancer and gastrointestinal stromal tumor cells demonstrate that the 2,3-diphenyl-1,6-naphthyridine-5-one derivative of formula (1a) is a cell permeable effector of Akt in various cancer cell lines.

These observations introduce the prospect of utilizing the 2,3-diphenyl-1,6-naphthyridine-5-one derivatives for the development of covalently modulating anticancer drugs particularly for tumors with aberrantly activated Akt, and further medicinal chemistry approaches.

EXAMPLE 13: BIOCHEMICAL ANALYSIS OF AKT KINASE INHIBITION

The inhibitory potencies of 14 substances towards inhibition of wild-type Akt1 and against the cancer-relevant mutant Akt1_E17K were determined, as described in Example 6, wherein the only difference in the experimental setup was the utilization of an ECHO520 Liquid Handling System (Labcyte Corp.) for the preparation of compound dilution series instead of manual preparation. The full length Akt1 protein harboring the E17K mutation was purchased from Biozol. The replacement of a glutamate by a lysine at position 17 not only results in over activation of the protein kinase, but is also accompanied by the resistance against reversible allosteric inhibitors, as shown for reference molecule MK-2206. However, ATP-competitive Akt inhibitors, e.g. GDC-0068 (Selleckchem), do not exhibit reduced potencies against this mutant form of Akt.

The following Table 3 shows the half-maximal inhibitory concentrations (IC$_{50}$) of the compounds according to formulas (1a), (28) to (33), (36), (45), (46), (47), (48), (49) and (50) and for the Akt inhibitors MK-2206 and GDC-0068 for wild-type Akt1 and against the mutant Akt1_E17K:

TABLE 3 half-maximal inhibitory concentrations (IC$_{50}$) against wild-type Akt1 and Akt1_E17K:

| Compound | Akt1 IC$_{50}$/nM | Akt1_E17K IC$_{50}$/nM |
| --- | --- | --- |
| 28 | 242.8 ± 5.3 | — |
| 29 | 387.0 ± 73.3 | 28103 ± 2888 |
| 30 | 8.9 ± 0.6 | 1951 ± 162 |
| 31 | 66.7 ± 3.7 | 8768 ± 797 |
| 32 | 1.5 ± 0.2 | 525 ± 43 |
| 1a | 0.4 ± 0.0 | 80 ± 10 |
| 33 | 0.7 ± 0.2 | 116 ± 18 |
| 45 | 13.7 ± 2.4 | 23678 ± 3600 |
| 36 | 10.7 ± 0.7 | 1843 ± 121 |
| 46 | 3.0 ± 0.3 | 952 ± 102 |
| 47 | 21.3 ± 1.8 | 2895 ± 137 |
| 48 | 8.1 ± 0.4 | 397 ± 172 |
| 49 | 4.1 ± 1.2 | 166 ± 41 |
| 50 | 87.6 ± 13.5 | 2872 ± 1462 |
| GDC-0068 | 2.6 ± 0.5 | 2 ± 1 |
| MK-2206 | 6.5 ± 0.8 | 3489 ± 434 |

As can be seen in Table 3, for covalent-allosteric Akt inhibitors, the impairment of inhibition was less significant than for reversible allosteric inhibitors. Therefore, the compounds of the invention might represent a new strategy to overcome resistance and effectively and selectively address Akt1_E17K.

When compared to Tables 1 and 2, differences in IC$_{50}$ values originate in the application of the contact-free, acoustic liquid handling system ECHO 520 (Labcyte), which was used for preparation of compound dilution series.

EXAMPLE 14: DETERMINATION OF KINETIC PARAMETERS (K$_i$, k$_{inact}$) TOWARDS WILD-TYPE AKT1 AND MUTANT AKT1_E17K The kinetic characterization of the compounds was performed as described in Example 8, wherein the only difference in the experimental setup was the utilization of an ECHO520 Liquid Handling System (Labcyte Corp.) for the preparation of compound dilution series instead of manual preparation. The following Table 4 shows the kinetic parameters (K$_i$, k$_{inact}$) of the 2,3-diphenyl-1,6-naphthyridine-5-one derivatives according to formulas (1a), (30) to (33), (36), (45) and (46) towards Akt1:

TABLE 4

Kinetic parameters K$_i$, k$_{inact}$, and k$_{inact}$/K$_i$ for covalent inhibitors on activated full-length Akt1:

| Compound | K$_i$/nM | k$_{inact}$/min$^{-1}$ | k$_{inact}$/K$_i$/µM$^{-1}$ s$^{-1}$ |
| --- | --- | --- | --- |
| 30 | 18.9 ± 8.7 | 0.123 ± 0.023 | 0.126 ± 0.054 |
| 31 | 67.1 ± 5.5 | 0.054 ± 0.006 | 0.013 ± 0.001 |
| 32 | 4.6 ± 1.9 | 0.134 ± 0.030 | 0.530 ± 0.162 |
| 1a | 1.0 ± 0.2 | 0.116 ± 0.021 | 1.693 ± 0.191 |
| 33 | 2.0 ± 0.5 | 0.110 ± 0.023 | 0.934 ± 0.074 |
| 45 | 45.4 ± 8.5 | 0.109 ± 0.023 | 0.041 ± 0.009 |
| 36 | 20.2 ± 3.3 | 0.061 ± 0.013 | 0.051 ± 0.010 |
| 46 | 10.7 ± 1.3 | 0.121 ± 0.016 | 0.190 ± 0.025 |

As can be seen in Table 4, the kinetic characterization of the compounds of the invention revealed differences in the formation of the reversible enzyme-inhibitor complex (IQ as well as in the formation of the covalent bond (k$_{inact}$) between the reactive cysteines 296 and 310 and the warhead moiety of the compounds of the invention. For the most potent inhibitors of formulas 1a, 30, 32, 33 and 46 comparable rates of irreversible enzyme inactivation were observed in a range from 0.110-0.134 µM$^{-1}$ s$^{-1}$, whereas more strongly pronounced differences in the dissociation constants (K$_i$) could be observed (1.0-18.9 nM). Thus, the inhibitory efficiency of compounds of the invention seems to depend more on the initial and reversible binding of the ligand to the enzyme than on the rate of irreversible adduct formation.

When compared to FIG. 6, differences in the kinetic parameters K$_i$, k$_{inact}$ and k$_{inact}$/K$_i$ values originate in the application of the contact-free, acoustic liquid handling system ECHO 520 (Labcyte), which was used for preparation of compound dilution series.

In addition, Table 5 shows the kinetic parameters (K$_i$, k$_{inact}$) of the 2,3-diphenyl-1,6-naphthyridine-5-one derivatives according to formulas (1a) and (33) towards mutant Akt1_E17K.

TABLE 5

Kinetic parameters K$_i$, k$_{inact}$, and k$_{inact}$/K$_i$ for covalent inhibitors on activated full-length mutant Akt1_E17K:

| Compound | K$_i$/nM | k$_{inact}$/min$^{-1}$ | k$_{inact}$/K$_i$/µM$^{-1}$ s$^{-1}$ |
| --- | --- | --- | --- |
| 1a | 94 ± 12 | 0.129 ± 0.024 | 0.023 ± 0.003 |
| 33 | 139 ± 21 | 0.105 ± 0.016 | 0.013 ± 0.002 |

As can be seen in Table 5, the two most potent inhibitors of formulas (1a) and (33) exhibit similar inactivation rates (k$_{inact}$) towards mutant Akt1-E17K (0.129 s$^{-1}$ and 0.105 s$^{-1}$, respectively) as towards wild-type Akt1 (0.116 s$^{-1}$ and 0.110 s$^{-1}$, respectively). However, the reduced affinities (K$_i$) for the mutant Akt1_E17K protein (94 nM and 139 nM, respectively) result in the significant loss in biochemical potency (IC$_{50}$) against Akt1_E17K. These results are in good agreement with the more pronounced loss in potency for reversible inhibitors, as these ligands solely depend on their affinity towards the target protein

EXAMPLE 15: EVALUATION OF PHARMACOKINETIC PARAMETERS IN A MOUSE MODEL

The lead compound 1a, which exhibited the best IC$_{50}$ (at 1 h pre-incubation time) as well as the highest affinity for Akt1 (K$_i$) and a reasonable reactivity (k$_{inact}$), was evaluated in mouse models in order to determine the maximum tolerated dose (MTD) and pharmacokinetic (PK) parameters. Therefore, increasing concentrations of compound 1a dissolved in PBS/PEG200 (60:40) were injected intraperitoneally (i.p.) into RjOrl:SWISS mice (Janvier Labs) resulting in an MTD of 20 mg/kg. For PK profiling, CD1 mice were treated intravenously (i.v.) using 2 mg/kg, intraperitoneally (i.p.) using 20 mg/kg and perorally (p.o.) using 20 mg/kg, respectively, with probe compound 1a. Blood samples were collected after 5, 15, 45 and 135 minutes and the plasma was separated by centrifugation at 15000×g, 4° C. for 10 minutes. EDTA was added to plasma in order to prevent blood from coagulation. The compound concentrations in the particular plasma samples were determined by LC-MS/MS, as follows:

Samples and blanks were prepared by adding 2.5 µL blank DMSO and 80 µL of ice-cold acetonitrile containing the internal standard (Griseofulvin, 1 µM) to 20 µl plasma followed by centrifugation at 13000 rpm (4° C.) for 10 min. 65 µL of the supernatant were diluted with 65 µL of LC-MS grade water. Samples were filtered (Millipore MSRLN0450 hydrophil) and subjected to LC-MS measurement. Analyte stock solution (10 mM in DMSO) was diluted in DMSO to yield DMSO stock solutions with the following concentrations: 10, 5, 2.5, 1, 0.5, 0.25, 0.1, 0.05, 0.025, 0.01, 0.005, 0.0025 µM. 2.5 µL of the corresponding DMSO stock solution were added to 20 µL of blank plasma followed by the addition of 80 µL of ice-cold acetonitrile containing the internal-standard. The samples were centrifuged for 10 min and 4° C. at 13000 rpm. 65 µL of the supernatant were diluted with 65 µL of LC-MS grade water and subjected to LC-MS analysis. A set of 3 different QCs (n=3) was prepared by adding of 2.5 µL DMSO stock solution (5, 0.5 and 0.05 µM) to 20 µL of plasma. Samples were subsequently handled as described above. All samples were analyzed using a Shimadzu LC20ADXR Solvent Delivery Unit, a Shimadzu SIL30ACMP autosampler and a ABSciex Qtrap5500 LC-MS/MS system. Therefore, 2 µL of sample were injected and separated using an Agilent Poroshell C18, 2.7 µm column (2.1 mm×50 mm) at 60° C. starting at 5% of solvent B for 0.3 min followed by a gradient up to 100% of solvent B over 0.6 min (flow rate 1 mL/min) with 0.1% formic acid in water as solvent A and 0.1% formic acid in acetonitrile as solvent B. Data evaluation was performed using Analyst 1.6.2 Software (Sciex).

Figure 10:
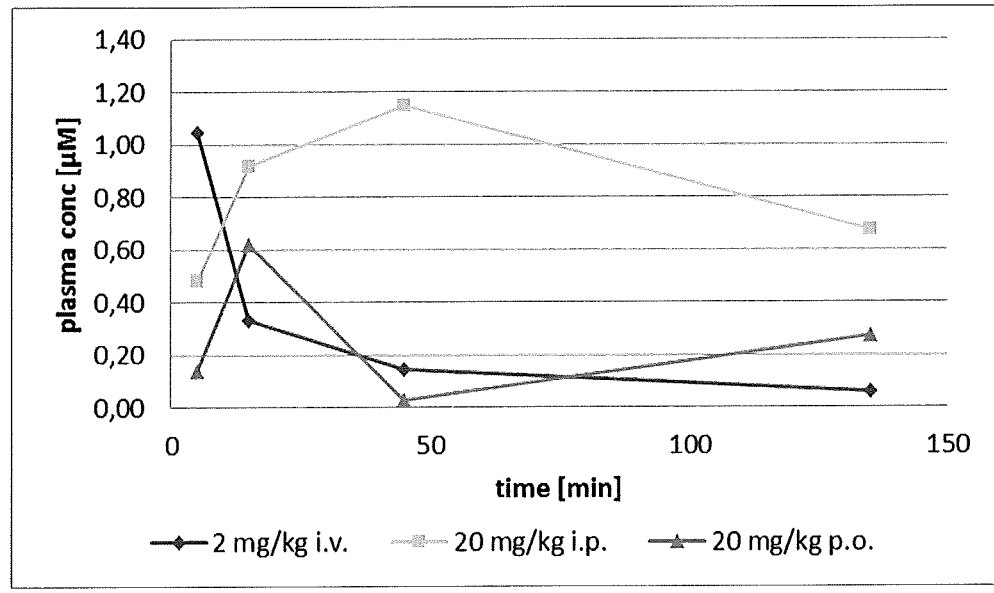
FIG. 10 shows the concentration time profiles after intravenously (i.v., 2 mg/kg), intraperitoneally (i.p., 20 mg/kg) and perorally (p.o., 20 mg/kg), respectively, injection of a mouse with the 2,3-diphenyl-1,6-naphthyridine-5-one derivative of formula (1a).

The FIG. 10 shows the respective concentration time profiles. As can be taken from FIG. 10, the concentration time profiles revealed maximum plasma concentrations of the compound of formula (1a) immediately after injection (i.v., 1.05 µM), after 45 min (i.p., 1.15 µM) and after 15 min (p.o., 0.62 µM). These findings illustrate a good bioavailability (p.o. 10.8%; or i.p. 47.7%).

EXAMPLE 16: PROTEIN X-RAY CRYSTALLOGRAPHY

For both validation and visualization of the anticipated binding mode of the compounds, protein X-ray crystallography was performed. Therefore, Akt1 was co-crystallized in the presence of the compound of formula (1a) and the obtained crystals were analyzed at the Swiss Light Source (Paul Scherrer Institut, Villingen). The collected diffraction data were processed with XDS and scaled using the program Scala. The complex crystal structure was refined to a resolution of 2.5 Å.

Figure 11:
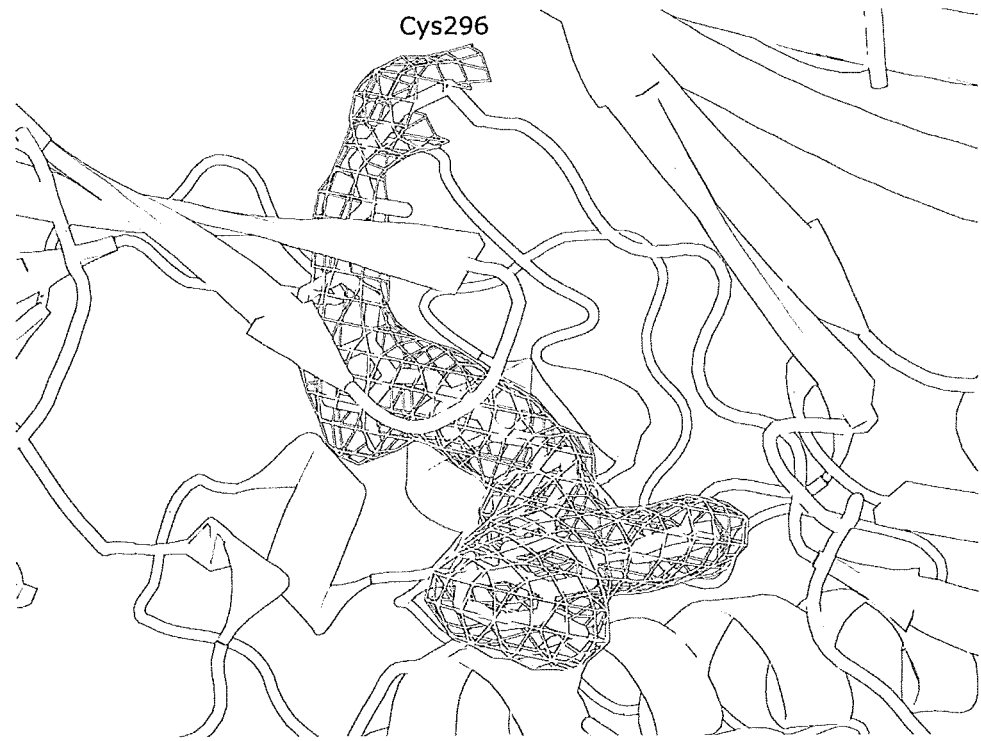
FIG. 11 shows the crystal structure refined to a resolution of 2.5 Å of Akt1 co-crystallized in the presence of the 2,3-diphenyl-1,6-naphthyridine-5-one derivative of formula (1a).

The FIG. 11 shows the crystal structure refined to a resolution of 2.5 Å of Akt1 co-crystallized in the presence of the compound (1a). FIG. 11 confirms a covalent bond formation of the 2,3-diphenyl-1,6-naphthyridine-5-one derivative of formula (1a) to the side chain of Cys296.

The invention claimed is:

1. A 2,3-diphenyl-1,6-naphthyridine-5-one derivative, wherein the 2,3-diphenyl-1,6-naphthyridine-5-one derivative is formula (1a) and/or racemates, enantiomers, stereoisomers, solvates, hydrates, and pharmaceutically acceptable salts and/or esters thereof:

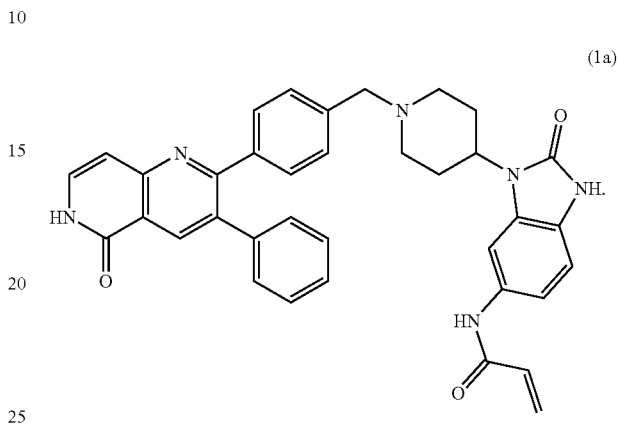

(1a)

2. A method of treating comprising administering to a subject a therapeutically effective amount of the 2,3-diphenyl-1,6-naphthyridine-5-one derivative according to claim 1.

3. A method of treating solid tumors comprising administering to a subject a therapeutically effective amount of the 2,3-diphenyl-1,6-naphthyridine-5-one derivative according to claim 1, wherein the solid tumors are selected from the group consisting of breast cancer, prostate cancer, colorectal cancer, ovarian cancer, thyroid cancer, lung cancer, liver cancer, pancreatic cancer, gastric cancer, melanoma, skin cancer, lymphoma and glioma.

4. A pharmaceutical composition comprising as an active ingredient a 2,3-diphenyl-1,6-naphthyridine-5-one derivative according to claim 1.

5. A method of treating blood cancer, comprising administering to a subject a therapeutically effective amount of the pharmaceutical composition according to claim 4.

6. A method of treating solid tumors comprising administering to a subject a therapeutically effective amount of the pharmaceutical composition according to claim 4, wherein the solid tumors are selected from the group consisting of breast cancer, prostate cancer, colorectal cancer, ovarian cancer, thyroid cancer, lung cancer, liver cancer, pancreatic cancer, gastric cancer, melanoma, skin cancer, lymphoma and glioma.

7. A method of treating blood cancer the method comprising the step of administering to a subject a therapeutically effective amount of a 2,3-diphenyl-1,6-naphthyridine-5-one derivative according to claim 1.

8. A method of treating solid tumors, the method comprising the step of administering to a subject a therapeutically effective amount of a 2,3-diphenyl-1,6-naphthyridine-5-one derivative according to claim 1, wherein the solid tumors are selected from the group consisting of breast cancer, prostate cancer, colorectal cancer, ovarian cancer, thyroid cancer, lung cancer, liver cancer, pancreatic cancer, gastric cancer, melanoma, skin cancer, lymphoma and glioma.

* * * * *